US011078507B2

(12) United States Patent
Kvist et al.

(10) Patent No.: US 11,078,507 B2
(45) Date of Patent: *Aug. 3, 2021

(54) PROBABILITY-DIRECTED ISOLATION OF NUCLEOTIDE SEQUENCES (PINS)

(71) Applicant: Samplix ApS, Herlev (DK)

(72) Inventors: Thomas Kvist, Roskilde (DK); Marie Just Mikkelsen, Brønshøj (DK)

(73) Assignee: Samplix ApS, Herlev (DK)

( * ) Notice: Subject to any disclaimer, the term of this patent is extended or adjusted under 35 U.S.C. 154(b) by 281 days.

This patent is subject to a terminal disclaimer.

(21) Appl. No.: 16/238,753

(22) Filed: Jan. 3, 2019

(65) Prior Publication Data

US 2019/0233865 A1 Aug. 1, 2019

Related U.S. Application Data

(62) Division of application No. 14/653,795, filed as application No. PCT/EP2013/077844 on Dec. 20, 2013, now Pat. No. 10,214,759.

(30) Foreign Application Priority Data

Dec. 21, 2012 (DK) .......................... PA 2012 70822

(51) Int. Cl.
*C12Q 1/68* (2018.01)
*C12P 19/34* (2006.01)
*C12Q 1/6848* (2018.01)
*C12Q 1/686* (2018.01)

(52) U.S. Cl.
CPC .............. *C12P 19/34* (2013.01); *C12Q 1/686* (2013.01); *C12Q 1/6848* (2013.01)

(58) Field of Classification Search
None
See application file for complete search history.

(56) References Cited

U.S. PATENT DOCUMENTS 10,214,759 B2 * 2/2019 Kvist .................. C12P 19/34
2003/0228586 A1 12/2003 Sekaly et al.

FOREIGN PATENT DOCUMENTS

WO 2004/058987 7/2004
WO 2008/096923 8/2008

OTHER PUBLICATIONS

Milbury et al. (Nucleic Acids Research, 2011 39(1):e2, p. 1-10) (Year: 2011).*
Zhang et al. (BMC Bioinformatics, 2004, vol. 5, p. 1-8) (Year: 2004).*
Altschul, S.F. et al., "Basic local alignment search tool," J. Mol. Biol. (1990) 215(3):403-410.
Chandler, D.P., "Redefining relativity: quantiative PCR at low template concentrations for industrial and environmental microbiology," J. Industrial Microbiology and Biotechnology, Basingstoke, GB (1998) 21(3):128-140.
Chenna, R. et al., "Multiple sequence alignment with the clustal series of programs," Nucl. Acids. Res. (2003) 31(13) 3497-3500.
Ellison, S. et al., "Routes to improving the reliability of low level DNA analysis using real-time PCR," BMC Biotechnology, Biomed Central Ltd., London (2006) 6(1):33.
Erlandsson, L. et al., "Amp-PCR: combining a random unbiased PHI29-amplification with a specific real-timem PCR, performed in one tube to increase PCR sensitivity," PLoS One (2010) 5(12):e15719.
Galm, U. et al., "Natural product drug discovery: the time have never been better," Chem & Biol. (2007) 14.
Harvey, A.L., "Natural products in drug discovery," Drug Discovery Today (2008) 13(19/20).
Hughes, S. et al., Whole Genome Amplification: Methods Express, Royal College of General Practitioners (2005) Methods and Approaches, p. 5.
Holetsky, A. et al., "Identification of methicillin-resistant *Staphylococcus aureus* carriage in less than one hour during a hostpital surveilance program," Clin. Infect. Dis. (2005) 40(7):976-81.
Kilstrup, M. et al., "Rapid genome walking: a simpliffced oligocassette mediated polymerase chain reaction using a single genome-specific primer," Nucl. Acid. Res. (2000) 28(11).
Kralik, P. et al., "development of a predictive model for detection of *Mycobacterium avium* susp. *paratuberculosis* in faeces by quantitative real time PCT," Veterinary Microbiology (2011) 149:133-138, 133-135; tables 1-3.
Kvist, T. et al., "Diversity of thermophilic and non-thermophilic crenarchaeota at 80 degrees," C. Fems Microbiol. Letter (2005) 244(1):61-68.
Kvist, T. et al., "Specific single-cell isolation and genomic amplification of uncultured microorganisms," Appl. Microbiol. Biotechnol., Springer-Verlag (2006).
Lasken, R.S. et al., "Multiple displacement amplification of genomic DNA," in Whole Genome Amplification, S. Hughes, Editor (2005), Scion Publishing Ltd., Oxfordshire, p. 99-118.
Liu, L. et al., "Comparison of next-generation sequencing systems," J. Biomed. Biotech. (2012) 251364.
Lorenz, P. et al., "Metagenomics and industrial applications," Nature Reviews—Microbiology (2005) 3:510-516.

(Continued)

*Primary Examiner* — Stephanie K Mummert
(74) *Attorney, Agent, or Firm* — Casimir Jones, S.C.; Melissa E. Karabinis

(57) ABSTRACT

The present invention pertains to an in vitro method in which the frequency of the targeted nucleotide sequence containing the DNA fragment of interest is increased stepwise, by several rounds of 1) dilution of a sample containing the DNA fragment of interest into several replicates (separation), 2) randomly amplifying DNA in the replicates (concentration), 3) detecting the DNA fragment of interest in at least one of the diluted and amplified replicates (selection) and repeating steps 1) through 3) until the DNA fragment of interest can be sequenced by standard sequencing techniques.

Figure 1:
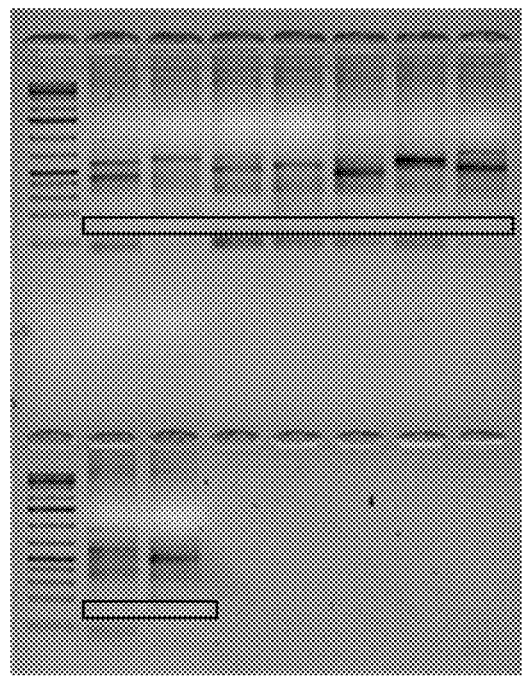

20 Claims, 8 Drawing Sheets
Specification includes a Sequence Listing.

(56) References Cited

OTHER PUBLICATIONS

Lukyanov, K.A. et al., "Molecule by molecule PCR amplification of complex DNA mixtures for direct sequencing: an approach to in vitro cloning," Nucl. Acids REs. (1996) 24(11):2194-2195.
Maurin, M., "Real-time PCR as a diagnostic tool for bacterial diseases," Exp. Rev. Mol. Diagn. (2012) 12(7):731-754.
Myers, L.E. et al., "Dilution assay statistics," J. Clin. Microbiol. (1994) 732-739.
Newman, D. et al., "Natural products as sources of new drugs over the period 1981-2002," J. Nat. Prod. (2003) 66:1022-1037.
Raghunathan, A. et al., "Genomic DNA amplification from a single bacterium," Appl. Envir. Microbiol. (2005) 71 (6):3342-3347.
Sambrook, J. et al., Molecular Cloning a Laboratory Manual (2001) Cold Spring Harbor Laboratory Press.
Shaw, J. et al., "Marker removal system for thermoanaerobacterium saccharolyticum and development of a markerless ethanologen," Appl. Environ. Microbiol. (2011) 2534-2536.
Shendure, J. et al., "Next-generation DNA sequencing," Nat. Biotech. (2008) 26(10):1135-1145.
Torsvik, V. et al., "High diversity in DNA of soil bacteria," Appl. Environ. Microbiol. (1990) 782-787.
Milbury, et al., "Ice-COLD-PCR enables rapid amplification and robust enrichment for low-abundance unknown DNA mutations." Nucleic Acids Research, 2011, 39(1): e2, p. 1-10.
Zhang, et al., "GOTree Machine (GOTM): a web-based platform for interpreting sets of interesting genes using Gene Ontology hierarchies." BMC Bioinformatics 2004, 5:16, p. 1-8.

\* cited by examiner

Figure 10

| EndoGlu-Fw<br>5' - GCACATTGCTGGTACAGAGATA - 3' [SEQ ID NO: 5] | EndoGlu-Re<br>5' - GATCTGCTTCCATTATGCTCTG - 3' [SEQ ID NO: 6]<br>(Reverse Complement to illustration) |
|---|---|
| ACGTTAA TAGGAACCAA TCACGCACAT TGCTGGTACA GAGATAGACT GACT TGAT<br>ACGTTAA TAGGAACCAA TCACGCACAT TGCTGGTACA GAGATAAACT TGAT<br>ACATTAA TAGGAACAAA TCACGCACAT TGCTGGTACA GAGATAAACT TGAG<br>ACGTTAA TAGGAACAAA TCACGCACAT TGCTGGTACA GAGATAAACT TGAG<br>ACNTTAA TAGGAAGNAA TCACGCACAT TGCTGGTACA GAGATANACT TGAN<br>*(shaded alignment rows)* | GAGAGATAAAT GCCC...............CGCTG<br>GAGAGATAAAT GCCCAGAGCA TAATGGAAGC AGATCCGCTG<br>GAGAGACAAT GCCCAGAGCA TAATGGAAGC AGATCCGCTG<br>GAGAGACAAT GCCCAGAGCA TAATGGAAGC AGATCCGCTG<br>GAGAGANAAT GCCCAGAGCA TAATGGAAGC AGATCCGCTG<br>*(shaded alignment rows)* |
| B-all-27f – bacterial 16S rRNA forward primer | Eub338r – bacterial 16S rRNA reverse primer |
| 5' - GAGTTTGATCCTGGCTCAG - 3' [SEQ ID NO: 7] | 5' - GCTGCCTCCCGTAGGAGT - 3' [SEQ ID NO: 8] |

PROBABILITY-DIRECTED ISOLATION OF NUCLEOTIDE SEQUENCES (PINS)

CROSS REFERENCE TO RELATED APPLICATIONS

This application is a divisional of U.S. patent application Ser. No. 14/653,795, filed Jun. 18, 2015, which is a national phase application under 35 U.S.C. 371 of PCT International Application No. PCT/EP2013/077844, filed Dec. 20, 2013, which claims priority to Danish Application No. PA 2012 70822, filed Dec. 21, 2012, each of which is herein incorporated by reference in its entirety and for all purposes.

TECHNICAL FIELD

The invention relates to a method for isolating a complex nucleotide fragment comprising a known nucleotide sequence element, i.e. a sequence encoding a conserved active site or domain, the method being applicable i.e. to high throughput screening for DNA fragments containing a known sequence element.

BACKGROUND OF THE INVENTION

General introduction

Molecular diagnostics and other DNA based approaches have gained increasing focus in sectors such as Discovery, R&D, and in various branches of diagnostics. However, whatever target is being analysed by assays or screening, all DNA based approaches face the same challenge, namely to generate sufficient amounts of available target relative to background DNA.

By increasing the presence of low abundance target DNA, at the expense of undesirable background DNA in a complex mixed DNA sample, traditional molecular methods, such as clone library construction, natural product discovery, PCR diagnostics, hybridizations, sequencing, metagenomics, and a variety of other molecular approaches are enabled.

The following describes methods currently used and the challenges of low abundance, mixed DNA samples.

PCR Diagnostics

In recent years, PCR tests have been extensively developed for routine diagnostics of infectious diseases in clinical microbiology. PCR is suited for rapid detection of bacteria directly in clinical specimens, allowing early, sensitive and specific laboratory confirmation of related diseases [1]. Moreover, it allows a rapid assessment of the presence of antibiotic resistance genes or gene mutations. An approach combining pathogen detection, their mechanisms of antibiotic resistance, their virulence factors and bacterial load in clinical samples could lead to profound changes in the care of these infected patients. Therefore, complex and multiplex PCR assays are currently being developed to enhance the field of molecular diagnostics.

However, PCR based diagnoses from mixed samples are often associated with challenges, as the presence of PCR products can arise from more than one DNA source in mixed complex samples. The presence of a specific antibiotic gene combined with the presence of specific bacterial strain does not necessarily mean that a resistant bacterial strain was present in the original sample. It only indicates that both a resistance gene and the bacterial strain were present in the sample, not necessarily that they arise from the same cell. Approaches to circumvent this problem have been suggested where the integration site of the antibiotic resistance gene was targeted by specific primers also known to target a specific bacterial strain. However, the exact integration site will then need to be known and this limits the use of the method.

DNA Sequencing

Knowledge of DNA sequences has become indispensable for basic biological research, and in numerous applied fields such as diagnostic, biotechnology, forensic biology, and biological systematics. The rapid speed of sequencing and decreasing cost attained with modern DNA sequencing technology has been instrumental in the sequencing of DNA sequences and the total amount of DNA sequenced worldwide is increasing rapidly.

While sequencing of pure samples is now standard procedure, sequencing of mixed samples of DNA is still challenging, costly and time consuming. When the target fragment is present at low frequency in a mixed nucleotide sample, for instance in a swab, faeces or blood sample, one must first make a clone or fragment library and then either sequence the complete library, or make smaller PCR fragments and sequence these. Sequencing of the complete library is expensive and time consuming and sequencing of PCR fragments is only possible if the sequence is already known to a very large extent and will return relatively short fragments which cannot be assigned to the same molecule or organism. If only part of the target sequence is known, PCR will not be possible and metagenome sequencing is needed.

There is therefore a need for a method for increasing the frequency of rare nucleotide molecules in a mixed sample of nucleotide molecules in order to decrease the cost and time of sequencing mixed samples.

Metagenomics

Metagenomics refers to a general sequencing approach, where a complex mixture of DNA is differentiated into small fractions and sequenced individually. The system does not rely on culturability and is, thus, applicable for both samples that can and cannot be cultivated in a laboratory.

Although metagenomics can be applied in some cases to describe complex samples, it is frequently the case that researchers prefer a specific subset of the genome or mixture of genomes, rather than the entire sequence of a sample or mixed sample of genomes [2]. Thus, there exists a strong need for flexible targeting methods that are matched to the individual requirements of the various techniques and studies. Although such techniques do exist they are often based on hybridization assays, and have the prerequisite of extensive sequence knowledge or have low sensitivity.

Therefore, a strong demand is present, for specific enrichment of a pre-defined sub-fraction of a complex mixture, if metagenomics is to be applied for analyzing rare/low abundance DNA fragments or targets.

Discovery

Different industries have different motivations to explore the vast resource that lies within uncultivated microbial diversity. Currently, white (industrial) biotechnology seems to play a central role in the establishment of the sustainable modern society. It is a commonly accepted assumption that only a small sub-fraction of the natural microbial biodiversity is available for screening. In 1990, Torsvijk et al. [3] estimated that at best only 1% of the naturally occurring microbial diversity of a soil sample could be cultivated under laboratory conditions. Hence, a huge potential lies within the discovery of yet unknown natural products, and also in biotechnological techniques that enable access to the unknown majority of DNA present in natural and environmental samples. Unfortunately, enormous amounts of sequencing is required if the otherwise unavailable information is to be retrieved.

Targeted enrichment of DNA fragments encoding industrially relevant proteins or enzymes would substantially decrease the required amount of sequencing.

SUMMARY OF THE INVENTION

The present invention provides in vitro method for enriching and/or isolating a target DNA molecule from a mixed polynucleotide sample comprising the steps:
a) providing a mixed polynucleotide sample containing said target DNA molecule, wherein said target DNA molecule comprises one or more unique consecutive sequence of at least 10 nucleotides,
b) serially diluting said mixed polynucleotide sample until the probability of detecting said target DNA molecule in a diluted sample is less than 0.75 preferably less than 0.50 or even more preferably less than 0.25, and
c) replicating a sufficient number of the diluted sample until the probability of detecting said target DNA molecule in at least one of the replicate dilution samples is at least 0.75 preferably 0.80 to 0.95;
d) amplifying the DNA in said replicate diluted samples to increase the abundance of the DNA in each sample;
e) detecting the presence or absence of said target DNA molecule in said replicate dilution samples amplified in step (d), wherein the frequency of said target DNA molecule in said replicate dilution sample is increased compared to the mixed polynucleotide sample in step (a);
f) serially diluting at least one replicate dilution sample containing said DNA molecule until the probability of detecting said target DNA molecule in a diluted sample is less than 0.75, and repeating steps (c) to (e) or (f) at least once.

LEGENDS TO THE FIGURES

FIG. 1:
The figure shows a 2% agarose gel of nine negative PCR reactions from the initial mixture. The boxed area indicates where a positive PCR product would be present in the gel. The PCR products outside the box are unspecific products and are disregarded in this context.

Figure 2:
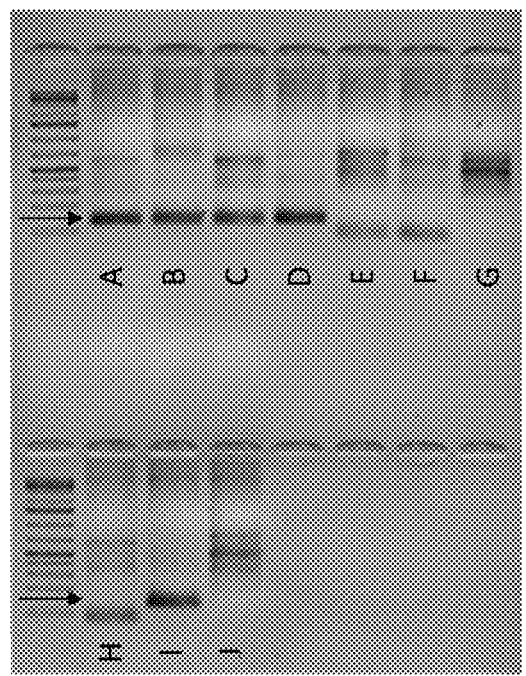

FIG. 2:
The figure shows a 2% agarose gel of ten PCR samples after the first round of
PINS. Five Samples (A, B, C, D, & I) contain PCR products of the expected size whereas the remaining five samples do not. The correct product size is arrowed in the gel (left). The PCR products in other locations (not arrowed) are unspecific products and are disregarded in this context.

Figure 3:
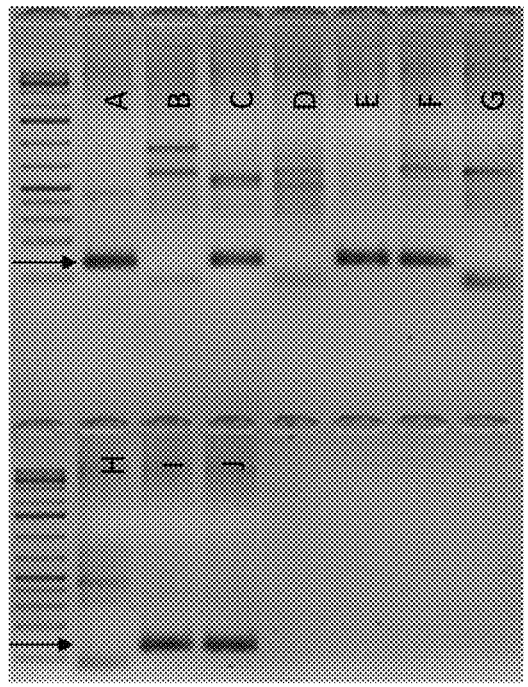

FIG. 3:
The figure shows a 2% agarose gel of ten PCR samples following the re-amplification of sample #10. Six samples (A, C, E, F, I, & 3) contain PCR products of the expected size whereas the remaining four samples do not. The correct product size is arrowed in the gel (left). The PCR products in other locations (not arrowed) are unspecific products and are disregarded in this context.

Figure 4:
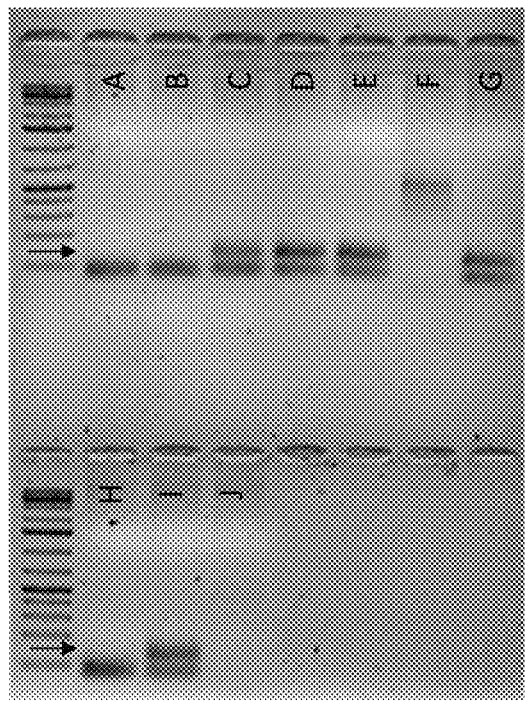

FIG. 4:
The figure shows a 2% agarose gel of ten PCR samples after the second round of PINS using 2E-1 dilution prior to PCR. Five Samples (C, D, E, G, & I) contain PCR products of the expected size whereas the remaining four samples do not. The correct product size is arrowed in the gel (left). The PCR products in other locations (not arrowed) are unspecific products and are disregarded in this context.

Figure 5:
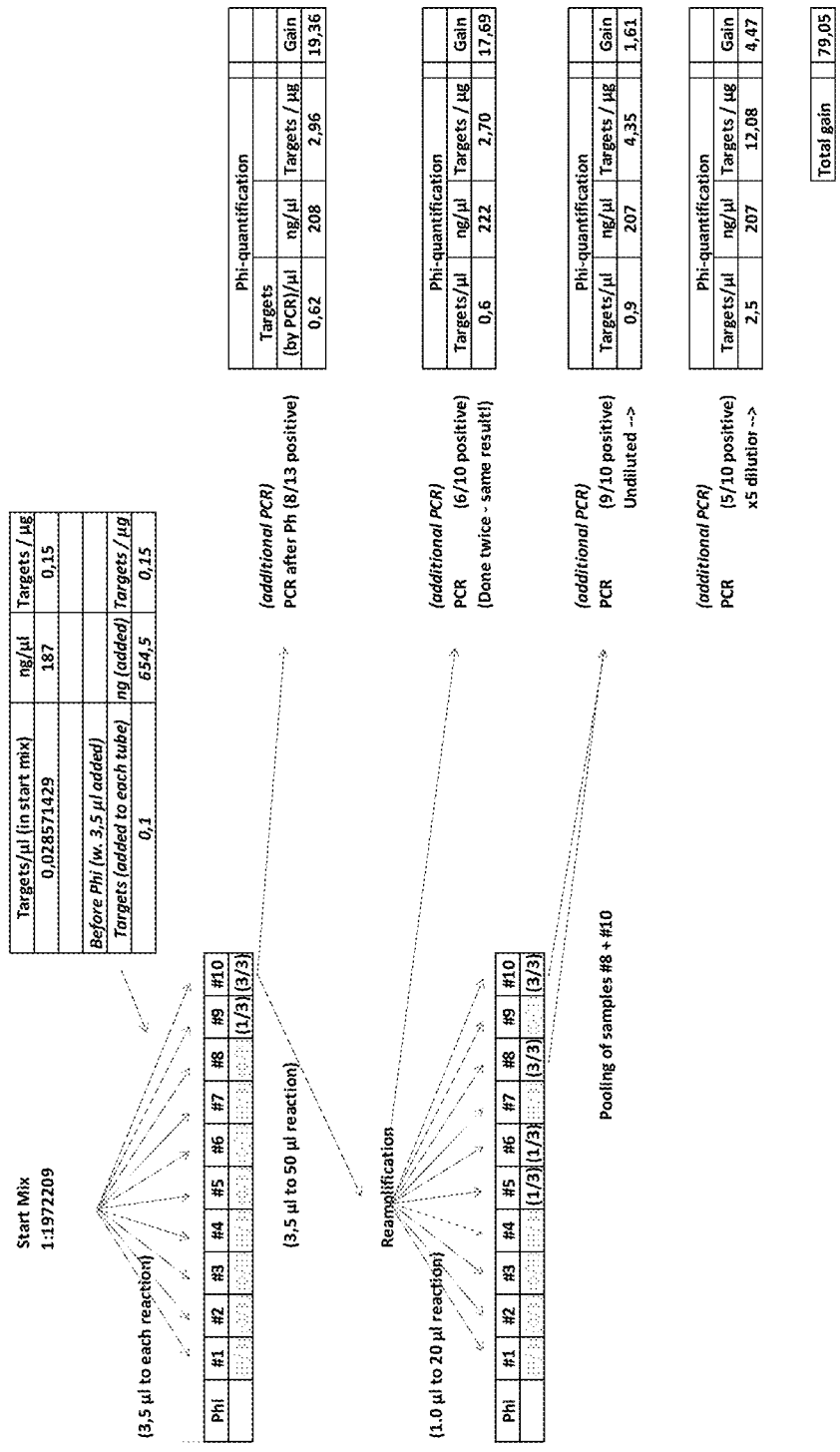

FIG. 5:
The figure shows a schematic illustration of two rounds of PINS with the following parameters:
A: The initial sample—with 0.028 ng/µl.
B: 10 Phi samples, created from A, using 3.5 µl "A" as template.
C: One sample with all 3 (of three) PCR products were positive.
D: Sample "C" re-amplified by using 3.5 µl sample #10 in a total reaction volume of 50.
E: 10 Phi samples, created from "D" using 1.0 µl as template in each reaction.
F & G: Two samples where all 3 (of three) PCR products were positive.
H: Pooling of samples "F" &"G"
I: Gain, calculated from initial concentration to the result after the first round of PINS.
J: Gain, calculated from first round of PINS to second round of PINS, using direct comparison at identical dilutions.
K: Gain, calculated from first round of PINS to second round of PINS, using comparison at different dilutions.
L: Gain, calculated from initial sample to finish (targets/ng).

Figure 6:
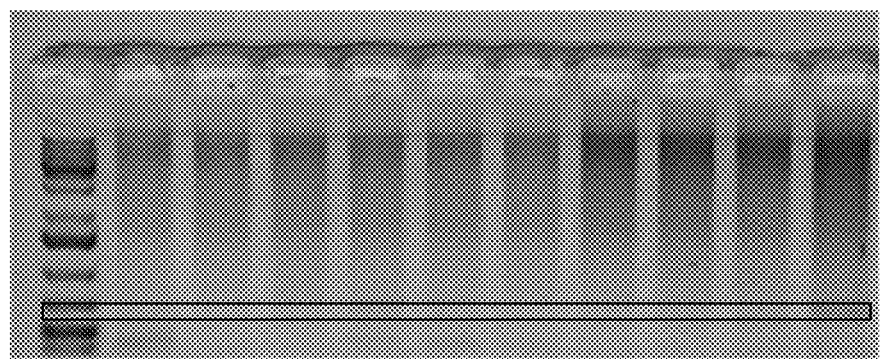

FIG. 6 The figure shows a 2% agarose gel of ten negative PCR reactions generated from an initial mixed polynucleotide sample comprising the target HPV18-DNA molecule. The boxed area indicates where a positive PCR product would be present in the gel. The PCR products outside the box are unspecific products and are disregarded in this context.

Figure 7:
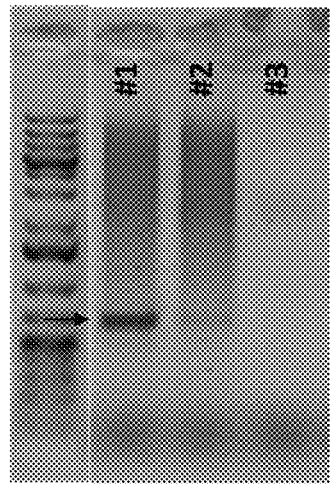

FIG. 7 The figure shows a 2% agarose gel of the products of three PCR designed to detect the presence of the target HPV18-DNA molecule. Lane #1 is a positive control PCR reaction; lane #2 is the PCR product of the PINS (MDA-mediate) enriched mixed polynucleotide sample containing 2.5 target copies/µl; and lane #3 is a negative PCR control. The arrow indicates the relative mobility of a DNA molecule of ~667 bp in the agarose gel.

Figure 8:
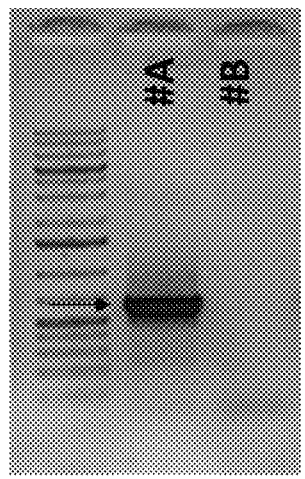

FIG. 8. The figure shows a 2% agarose gel of the PCR product obtained by re-amplification of the target HPV18-DNA molecule shown in FIG. 7. The arrow indicates the relative mobility of a DNA molecule of ~667 bp in the agarose gel FIG. 9 Alignment of the retrieved sequences for the PINS enriched target HPV18-DNA molecule with HPV18 sequence (HPU89349), showing that the sequence is perfectly aligned with zero mismatches.

FIG. 10. Primers and partial alignments of the sequences of retrieved microbial genes encoding endoglucanase.

Figure 11:
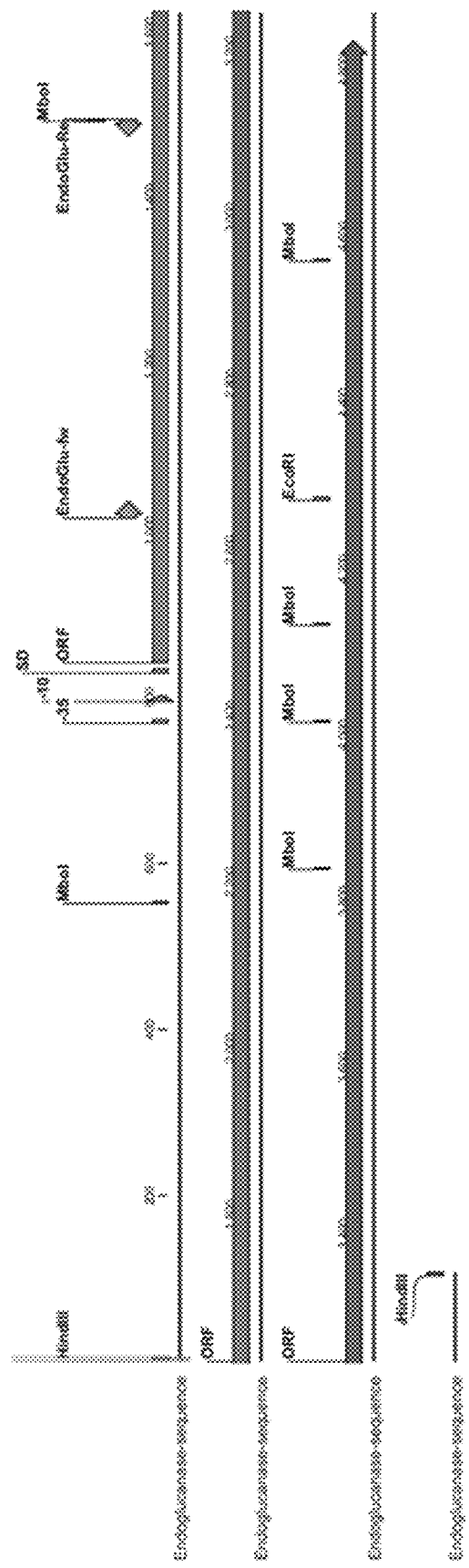

FIG. 11. The figure illustrates the nucleotide sequence of a gene encoding endoglucanase enriched by PINS. Restriction sites (MboI, EcoRI, and HindIII) used for RGW are inserted in boxes. −35 & −10 illustrates the position of the putative promoter location and SD is the position of the ShineDalgarno. EndoGlu-Fw & EndoGlu-Re are the primers used during PINS. ORF indicates the position of the open reading frame.

DETAILED DESCRIPTION OF THE INVENTION

The present invention pertains to an in vitro method in which the frequency of the targeted nucleotide sequence containing the DNA fragment of interest is increased stepwise, by several rounds of 1) dilution of a sample containing the DNA fragment of interest in several replicates (separation), 2) randomly amplifying DNA in the replicates (concentration), 3) detecting the DNA fragment of interest in at least one of the diluted and amplified replicates (selection) and repeating steps 1) through 3) until the DNA fragment of interest can be sequenced by standard sequencing techniques.

The invention is based on the principle that if a selected DNA fragment of interest, present in a mixed sample, is located at a dilution where the probability of finding it is small, the frequency of the DNA fragment of interest will be higher at that dilution than in the mixed sample, and its frequency can be further increased by rounds of selection (as above), until it can be sequenced by standard methods such as Sanger sequencing or Pyro sequencing or similar detection of DNA sequence or by PCR, hybridization or other detection assays.

The method of the invention is surprisingly efficient, whereby the extent of screening can be reduced from screening of hundreds of thousands of clones in a clone library according to traditional screening methods [17], to screening less than a few hundred DNA samples (Table 1).

TABLE 1

Efficiency of PINS

| Prevalence | PINS (no. of tests) | Traditional (no. of tests) | Screening Improvement |
|---|---|---|---|
| $1/10^4$ | 88 | 10,000 | 114x |
| $1/10^5$ | 108 | 100,000 | 909x |
| $1/10^6$ | 128 | 1,000,000 | 7,692x |
| $1/10^7$ | 148 | 10,000,000 | 66,667x |
| $1/10^5$ | 168 | 100,000,000 | 588,235x |
| $1/10^9$ | 188 | 1000,000,000 | 5,263,158x |

Each cycle of PINS provides an estimated 10× increase in the prevalence of the genetic element of interest. The number of tests required to increase the prevalence from the starting level to the desired ending level can be calculated, i.e. 78 tests are required to increase the prevalence from $1/10^6$ to $1/10^2$ (based on estimated 10×/cycling).

I: PINS

The essential steps of the in vitro PINS method are further described below:

a) A sample of Mixed Polynucleotides Comprising a Target DNA Molecule

A sample of mixed polynucleotides known to comprise a target DNA molecule, is selected for performing PINS. One or more nucleotide sequences of at least 10 (or 15) unique nucleotides located within the target DNA molecule is selected for screening and detecting the DNA molecule by a desired method, such as PCR detection, DNA detection with hybridization probes or similar. Typically, the frequency of the target DNA molecule sample of mixed polynucleotides is less than $10^{-2}$, it may for example lie between $10^{-3}$ and $10^{-7}$.

b) Primary Dilution of the Mixed Polynucleotide Sample

The mixed polynucleotide sample is serially diluted by a desired number of dilutions until the probability of detecting the target DNA molecule in a diluted sample is less than 0.75, (this sample is designated dilution (N)). Serial dilutions preferably have a dilution factor of greater than 1:1, preferably between 1:2 to 1:20, e.g., 1:10. Each diluted sample is placed in a separate container, such as a well in a microtiter plate, a plastic tube or similar.

Various methods may be used to identify sample (N) in the dilution series in which the probability of detecting the target DNA molecule is less than 0.75. For example, the serial dilutions of the mixed polynucleotide sample may be amplified to increase the abundance of the DNA in each sample, followed by the step of detecting the presence or absence of said target DNA molecule in each amplified sample. The most dilute sample within the dilution series in which the target DNA molecule can be detected is designated "P". The next dilution in the dilution series, designated "N", is the least diluted sample in the dilution series where the target DNA molecule cannot be detected. The dilution factor of "N" relative to the DNA sample in a) is designated Dt, and the dilution factor between P and N is designated, D.

Alternatively, the frequency and abundance of the target DNA molecule in the mixed polynucleotide sample may be determined by real time PCR, from which the dilution required to prepare sample (N) can be calculated (see example 1).

Alternatively, the target DNA molecule may be detected by hybridization based assays or by assays detecting an RNA or protein product of the target sequence.

c) Creating Replicate Dilution Samples Having Dilution N

A sufficient number of replicates of the diluted sample (N) are generated until the probability of detecting the target DNA molecule in at least one of the replicate dilution samples is one. A suitable number of replicates lies between 2 and 500, preferably at least 10-20 replicates. Typically, a suitable number of replicates will correspond to the dilution factor used to create the dilution series, i.e. if the dilution factor is 1:10, then about 10 replicates should be sufficient. Each diluted sample is placed in a separate container, such as a well in a microtiter plate, a plastic tube or similar.

d) Genomic DNA Amplification

DNA in each replicated diluted sample is amplified using any method of total DNA amplification to increase the abundance of the DNA in each sample. Suitable amplification methods including Degenerate Oligonucleotide Primed PCR (DOP-PCR), Multiple Displacement Amplification (MDA) [4], randomly primed PCR or similar.

e) Screening the Replicate Dilution Sample (+/−) for Target DNA

The replicate samples (N) following genome amplification in step d) are screened for the presence of the target DNA molecule using the desired detection technique. In at least one or more screened samples that are shown to contain the target DNA molecule (sample+), the frequency of the target DNA molecule will be increased compared to its frequency in the mixed polynucleotide sample in step (a).

One or more of these samples+ are then serially diluted until the probability of detecting the target DNA molecule in a diluted sample is less than 0.75. Typically, the total dilution of this sample is Dt increased by factor D.

Using this sample the steps (c) to (e) are repeated at least once, preferably until the target DNA molecule has been amplified to an extent where the nucleotide sequence of the target DNA molecule or parts thereof can be readily sequenced, as described below in f). The number of repetitions of steps (c) to (e) is generally at least 1, but is more likely to require 2, 3, 4, 5 or 6 or more repetitions, whereby the eventual frequency reached of the target DNA molecule is greater than $10^{-3}$, preferably greater than $10^{-1}$.

f) Characterization of the Enriched Target DNA Molecule.

Once the frequency of the target DNA molecule is sufficiently increased, the DNA can be subjected to direct DNA sequencing. Sequencing of the target DNA molecule; both the PCR amplified target DNA fragment used for detection and the nucleotide sequences flanking the 5' and 3' direction of the target DNA fragment, is implemented using the desired DNA sequencing method, such as Sanger sequencing, pyro sequencing or similar methods.

An example of how the PINS method may be implemented is set out in Table 2.

Scheme for Performing PINS

Original DNA Sample Designated Sample N0

Make 10-fold dilutions of Sample N0 in wells A1-A8 of a microtiter plate. Perform MDA (optionally): N0->N0$^{mDA}$. Transfer aliquots of N0->N0$^{MDA}$ to PCR plate and perform PCR to detect target DNA molecule.

TABLE 2

| Dilution plate | PCR | PCR Plate | Dilution plate | PCR | PCR plate |
|---|---|---|---|---|---|
| N0 × 10-0$^{A1}$ | -> | P | N0$^{MDA}$ × 10-0$^{A1}$ | -> | P |
| N0 × 10-1$^{A2}$ | | P | N0$^{MDA}$ × 10-1$^{A2}$ | | P |
| N0 × 10-2$^{A3}$ | | P | N0$^{MDA}$ × 10-2$^{A3}$ | | P |
| N0 × 10-3$^{A4}$ | | P | N0$^{MDA}$ × 10-3$^{A4}$ | | P |
| N0 × 10-4$^{A5}$ | | N | N0$^{MDA}$ × 10-4$^{A5}$ | | N |
| N0 × 10-5$^{A6}$ | | N | N0$^{MDA}$ × 10-5$^{A6}$ | | N |
| N0 × 10-6$^{A7}$ | | N | N0$^{MDA}$ × 0-6$^{A7}$ | | N |
| N0 × 10-7$^{A8}$ | | N | N0$^{MDA}$ × 10-7$^{A8}$ | | N |

Select N0×10-4$^{A5}$ or N0$^{mDA}$×10-4$^{A5}$=Sample N1

Make 20 replicate aliquots of sample N1 and add into A1-C4 on dilution Plate (Table 3). Perform MDA on all replicates to amplify total DNA in each replicate, followed by PCR to detect the target DNA molecule in the amplified DNA.

TABLE 3

| Cycle 1 |||||||||
|---|---|---|---|---|---|---|---|---|
| Dilution plate ||| MDA | MDA plate ||| PCR | PCR plate ||
| N1$^{A1}$ | N1$^{B1}$ | N1$^{C1}$ | -> | N1$^{A1+MDA}$ | N1$^{B1+MDA}$ | N1$^{C1+MDA}$ | -> | N N N |
| N1$^{A2}$ | N1$^{B2}$ | N1$^{C2}$ | | N1$^{A2+MDA}$ | N1$^{B2+MDA}$ | N1$^{C2+MDA}$ | | N N P |
| N1$^{A3}$ | N1$^{B3}$ | N1$^{C3}$ | | N1$^{A3+MDA}$ | N1$^{B3+MDA}$ | N1$^{C3+MDA}$ | | P N N |
| N1$^{A4}$ | N1$^{B4}$ | N1$^{C4}$ | | N1$^{A4+MDA}$ | N1$^{B4+MDA}$ | N1$^{C4+MDA}$ | | N N N |
| N1$^{A5}$ | N1$^{B5}$ | | | N1$^{A5+MDA}$ | N1$^{B5+MDA}$ | | | N N |
| N1$^{A6}$ | N1$^{B6}$ | | | N1$^{A6+MDA}$ | N1$^{B6+MDA}$ | | | N P |
| N1$^{A7}$ | N1$^{B7}$ | | | N1$^{A7+MDA}$ | N1$^{B7+MDA}$ | | | N N |
| N1$^{A8}$ | N1$^{B8}$ | | | N1$^{A8+MDA}$ | N1$^{B8+MDA}$ | | | N N |

Select (N1$^{A3+MDA}$+N1$^{B6+MDA}$+N1$^{C2+MDA}$) and dilute $10^{-5}$=Sample N2

Make 20 aliquots of sample N2 and add into A1-C4 on dilution plate (Table 4). Perform MDA on all replicates to amplify total DNA in each replicate, followed by PCR to detect the target DNA molecule in the amplified DNA.

TABLE 4

| Cycle 2 |||||||||
|---|---|---|---|---|---|---|---|---|
| Dilution plate ||| MDA | MDR plate ||| PCR | PCR plate ||
| N2$^{A1}$ | N2$^{B1}$ | N2$^{C1}$ | -> | N2$^{A1+MDA}$ | N2$^{B1+MDA}$ | N2$^{C1+MDA}$ | -> | N N N |
| N2$^{A2}$ | N2$^{B2}$ | N2$^{C2}$ | | N2$^{A2+MDA}$ | N2$^{B2+MDA}$ | N2$^{C2+MDA}$ | | N P N |
| N2$^{A3}$ | N2$^{B3}$ | N2$^{C3}$ | | N2$^{A3+MDA}$ | N2$^{B3+MDA}$ | N2$^{C3+MDA}$ | | N N N |
| N2$^{A4}$ | N2$^{B4}$ | N2$^{C4}$ | | N2$^{A4+MDA}$ | N2$^{B4+MDA}$ | N2$^{C4+MDA}$ | | N N N |
| N2$^{A5}$ | N2$^{B5}$ | | | N2$^{A5+MDA}$ | N2$^{B5+MDA}$ | | | P N |
| N2$^{A6}$ | N2$^{B6}$ | | | N2$^{A6+MDA}$ | N2$^{B6+MDA}$ | | | N N |
| N2$^{A7}$ | N2$^{B7}$ | | | N2$^{A7+MDA}$ | N2$^{B7+MDA}$ | | | N N |
| N2$^{A8}$ | N2$^{B8}$ | | | N2$^{A8+MDA}$ | N2$^{B8+MDA}$ | | | N N |

Select ($N2^{A5+MDA}+N2^{B2+MDA}$) and dilute $10^{-6}$=Sample N3

Make 20 aliquots of Sample N2 and add into A1-C4 on dilution plate (Table 5). Perform MDA on all replicates to amplify total DNA in each replicate, followed by PCR to detect the target DNA molecule in the amplified DNA.

TABLE 5

| Cycle 3 | | | | | | | | | |
|---|---|---|---|---|---|---|---|---|---|
| Dilution plate | | | MDA | MDA plate | | | PCR | PCR plate | |
| $N3^{A1}$ $N3^{B1}$ $N3^{C1}$ | | | -> | $N3^{A1+MDA}$ $N3^{B1+MDA}$ $N3^{C1+MDA}$ | | | -> | N N P | |
| $N3^{A2}$ $N3^{B2}$ $N3^{C2}$ | | | | $N3^{A2+MDA}$ $N3^{B2+MDA}$ $N3^{C2+MDA}$ | | | | N N N | |
| $N3^{A3}$ $N3^{B3}$ $N3^{C3}$ | | | | $N3^{A3+MDA}$ $N3^{B3+MDA}$ $N3^{C3+MDA}$ | | | | N P N | |
| $N3^{A4}$ $N3^{B4}$ $N3^{C4}$ | | | | $N3^{A4+MDA}$ $N3^{B4+MDA}$ $N3^{C4+MDA}$ | | | | N N N | |
| $N3^{A5}$ $N3^{B5}$ | | | | $N3^{A5+MDA}$ $N3^{B5+MDA}$ | | | | N P | |
| $N3^{A6}$ $N3^{B6}$ | | | | $N3^{A6+MDA}$ $N3^{B6+MDA}$ | | | | N N | |
| $N3^{A7}$ $N3^{B7}$ | | | | $N3^{A7+MDA}$ $N3^{B7+MDA}$ | | | | N N | |
| $N3^{A8}$ $N3^{B8}$ | | | | $N3^{A8+MDA}$ $N3^{B8+MDA}$ | | | | N N | |

Select ($N3^{B3+MDA}+N3^{B5+MDA}+N3^{C1+MDA}$) and determine the abundance of the target DNA molecule. If this is sufficient for analysis such as sequencing, the selected sample may be used directly; otherwise additional cycles of PINS can be applied.

II: Multiplex PINS

PINS can be adapted to perform multiplex PINS. Multiplex PINS employs additional features that are designed to detect a 2nd consecutive sequence of at least 10 (or 15) nucleotides in the sample of mixed polynucleotides analysed, by amplification of this 2nd consecutive sequence with sequence specific primers to generate a 2nd target DNA fragment. If the 1st and 2nd consecutive sequence co-purify, at each cycle of PINS, then they must be located on the same MDA-amplified target DNA molecule.

III Samples Analyzed by PINS and Multiplex PINS

III.i Sample of Mixed Polynucleotides

PINS may be applied to a sample of mixed polynucleotides known to comprise a target DNA molecule. A sample of mixed polynucleotides comprises a population of DNA molecules (e.g. chromosomal DNA molecules or plasmid DNA molecules) where the individual DNA molecules within the population differ with respect to a known consecutive sequence of at least 10 (or 15) nucleic acid base pairs in their DNA, such that a target molecule comprising the known consecutive sequence differs from and can be distinguished from non-target molecules in the sample. The sample of mixed polynucleotides may additionally comprise single stranded RNA or DNA polynucleotides. The population of DNA molecules in the sample of mixed polynucleotides comprises the target DNA molecule.

A target DNA molecule comprises one or more known consecutive sequence of at least 10 (or 15) unique nucleic acid base pairs (or nucleotides). A target DNA molecule can be selected from a sample of mixed polynucleotides, by selecting for a target DNA molecule comprising this consecutive sequence of at least 10 nucleic acid base pairs (or nucleotides). The target DNA molecule can also be selected from the sample of mixed polynucleotides, by selecting for a target DNA molecule comprising at least two consecutive sequences of at least 10 (or 15) nucleic acid base pairs (or nucleotides), wherein the two consecutive sequences are comprised within a DNA molecule of 50 to 100,000 nucleic acid base pairs, preferably 150 to 3,000 nucleic acid base pairs, more preferably 150 to 1500 nucleic acid base pairs.

The method of the invention is particularly suitable where the frequency of the target DNA molecule in the sample of mixed polynucleotides is less than $10^{-3}$.

The method of the invention is also suitable where the frequency of the target DNA molecule in the sample of mixed polynucleotides is $10^{-4}$, $10^{-5}$, $10^{-6}$, $10^{-7}$, or lower. In many instances, the sample of mixed polynucleotides will be derived from a cell population comprising genomic DNA, while in other instances, the sample may be derived from samples where the polynucleotides are of diverse origin, such as samples collected from nature. Irrespective of its source, the frequency of the target DNA molecule is defined as the number of genomes or genome equivalents containing the target DNA divided by the number of total genome equivalents. The frequency of the target DNA molecule in the sample of mixed polynucleotides is determined by making a dilution series in triplicate, detecting the presence or absence of target and determining the number of targets using, for instance, most probable number methods. The concentration of DNA is measured and the number of total genome equivalents is determined by dividing this concentration by the average molecular weight of the genome.

III.ii Source of the Sample of Mixed Polynucleotides

According to one embodiment of the present invention, the target DNA molecule is derived from the genome of a cell, where the genome may be either chromosomal or extrachromosomal DNA. Further, the target DNA molecule may be derived from a cell, where the cell is selected from amongst a microbial cell, a plant cell, an animal cell, or a mammalian cell. The mammalian cell may be a human cell. The microbial cell may be a bacterial cell, a yeast cell or a fungal cell.

Furthermore, the target DNA molecule may be derived from a fungal mycelium or fungal spores.

When the target DNA molecule is derived from one or more cell, the cell(s) may be part of a multicellular tissue or multicellular organism.

Furthermore, the target DNA molecule may be derived from one or more viral particles, where the virus has an RNA or DNA genome. Alternatively the target DNA molecule may be derived from a host genome comprising integrated DNA derived from a virus. The target DNA molecule may also be derived from a bacteriophage.

Irrespective of the derivation of the target DNA or RNA molecule, the target DNA or RNA molecule is present in a sample of mixed polynucleotides, where the mixed polynucleotides may be derived from a sample collected from nature, for example a sample of soil, water or air. Alternatively, the sample may be derived from a multicellular organism, such as a mammal, for example an animal or a human subject. When the sample is derived from a mammal, the sample (for example a biopsy) may be derived from a body fluid (e.g. blood, plasma, serum, lymph and urine), from faeces or from a body tissue or organ. The multicellular organism from which the sample is derived may be a living or may be a dead organism.

III.iii Preparation of the Sample of Mixed Polynucleotides

The sample of mixed polynucleotides comprising the target DNA molecule may be prepared from a sample collected from nature or from an organism (e.g. a biopsy). Methods for selective extraction of polynucleotides comprising DNA or RNA are known in the art [5]. When the target DNA molecule is derived from a cell, the step of cell disruption or cell permeabilisation is normally required in order to release total nucleic acid molecules (including DNA or RNA) from a cell, this step preceeding the subsequent step of selective extraction of polynucleotides comprising DNA or RNA.

Where the target DNA molecule is derived from an RNA genome, the RNA genome or parts thereof are first reverse transcribed to provide a cDNA molecule, where the nucleotide sequence of the cDNA corresponds to (is a reverse transcript of) the RNA genome.

IV Methods of Random Amplification of DNA Suitable for PINS

A range of different approaches have been suggested for general amplification of DNA, such as randomly degenerate primed PCR, linker ligation PCR, or, Degenerate Oligonucleotide Primed (DOP) PCR and Multiple Displacement Amplification (MDA). MDA has proven efficient in performing whole-genome amplification (WGA) of even very small amounts of DNA [6]. Compared with more traditional PCR-based WGA methods, MDA generates DNA molecules with a higher molecular weight, having better genome coverage. MDA employs a strand displacement polymerase that possesses two enzymatic activities: DNA synthesis (polymerase) and an exonucleolytic activity that degrades single stranded DNA in the 3'- to 5'-direction, as exemplified by bacteriophage phi29 DNA polymerase, that belongs to eukaryotic B-type DNA polymerases (UniProtKB/TrEMBL: Q38545). Other useful polymerases include BstI polymerase.

V Sequence Determination of the Target DNA Molecule

Isolation of the target DNA molecule by PINS is based on detection of one or more unique consecutive sequence of at least 15 nucleotides in said DNA molecule. When detection is based on PCR, where the one or more unique consecutive sequences are amplified to generate a target DNA fragment, the nucleotide sequence of this fragment can be determined. In addition, the nucleotide sequences flanking the target DNA fragment in the 5' and 3' direction can be determined by rapid genome walking (RGW)[7]. RGW is a simple, PCR-based method for determining sequences upstream or downstream in a larger DNA molecule starting from a known sequence, such as a target DNA fragment. RGW enables individual amplification of up to 6 kb in a large DNA molecule using PCR. The sequences can be extended simply by taking multiple cycles of RGW, using new primers based on the sequence obtained in previous cycles. Typically libraries are constructed from a purified sample of the large target DNA molecule, by digesting the DNA separately with four different restriction enzymes and ligating the products to a specially designed adaptor. The ligated DNA is then sequenced with primers annealing to the adaptors or to known sequences within the DNA, using the desired DNA sequencing method, such as Sanger sequencing, pyro sequencing, sequencing by synthesis, ligation or two base-coding sequencing or similar methods [8].

VI Application of PINS and Multiplex Pins

VI.i Research and Development Applications of PINS and Multiplex PINS

Use of PINS to isolate or enrich target DNA in mixed polynucleotide samples extracted from samples collected from nature, provides direct access to the genome, or parts thereof, of microorganisms that exist in nature and that frequently cannot be obtained as axenic cultures. PINS is particularly useful for isolating or enriching DNA encoding enzymes involved in producing chemical building blocks or active agents such as:

acids (such as maleic-, aspartic-, malonic-, propionic-, succinic-, fumaric-, citric-, acetic-, glutamic-, itaconic-, levulinic-, acotinic-, glucaric-, gluconic-, and lactic-acid), amino acids (such as serine, lysine, threonine), alcohols (ethanol, butanol, propanediol, butanediol, arabitol) and other high value products (such as acetoin, furfural, and levoglucosan)

antibiotics, anticancer compounds (e.g. peptide-polyketides; lactam analogues)

Thus PINS is particularly useful for isolation or enrichment of target DNA encoding enzymes selected among an oxidoreductase, transferase, hydrolase, lyase, isomerase or ligase. Multiplex PINS is particularly useful for isolation or enrichment of target DNA comprising an operon of two or more open reading frames encoding two or more enzymes, where the enzymes may be part of a multifunctional enzyme complex, as the technique can take advantage of high fidelity of polymerases (like Phi29) in the MDA amplification to generate large amplified DNA fragments of up to 100000 bp.

VI.ii Diagnostic Applications of PINS and Multiplex PINS

PINS or Multiplex PINS may be used to analyse target DNA in samples derived from multicellular organisms, such as biopsy or sample of body fluid or faeces obtained from a subject (e.g. human or animal subject), for the diagnosis or monitoring the progress of a medical indication or disease.

Diagnosis of a wide range of medical indications in a subject such as a disease caused by an infectious agent (e.g. micro-organism or virus) can be assisted by the isolation or enrichment and detection of a target DNA or RNA molecule that is derived from the genome of the infectious agent by PINS or Multiplex PINS, where the target DNA molecule is detected in a sample of mixed polynucleotides derived from a biopsy or sample of body fluid obtained from a patient.

Use of multiplex PINS in target DNA molecule isolation provides the additional feature, that additional diagnostic features of the disease can be determined. For example, where the genome of the infectious agent comprises resistance genes that confer resistance to certain therapeutic agents, co-enrichment of a resistance gene and a sequence describing the infectious agent in the PINS procedure will indicate that the infectious agent is carrying the resistance gene.

PINS or Multiplex PINS may also be used to assist diagnosis of a disease caused by, or originating from the presence of a viral agent in a subject. The presence and/or chromosomal integration of DNA that is derived from a viral genome, in a biopsy or sample of body fluid obtained from a patient can be detected by PINS by sequencing the entire DNA fragment comprising the viral DNA sequence. Using multiplex PINS the presence or absence of viral DNA at a known integration site can be determined by tracking the co-enrichment of the viral DNA and integration site DNA sequence.

VII PINS and Bias in Amplification

PINS is based on specifically selecting samples where amplification of a desired DNA region from a complex, mixed DNA sample has occurred. Although Phi29 based amplification (MDA) has been described repeatedly as the most reliable genome amplification currently available, it is known to introduce significant bias. Pan et al. [18] states in general terms that a highly specific whole genome amplification (WGA) of complex DNA pools which avoids amplification bias remains a challenge. Moreover, similar observations are seen with alternative amplification methods such as DOP-PCR and random priming PCR. These two amplification methods are described as being much less efficient at reproducing the locus representation [19], resulting in even more biased amplification products. While bias is seemingly unavoidable regardless of the amount of reaction template [20] present, the amount of template independent product (TIP) or bias introduced during amplification is seemingly correlated negatively to the amount of DNA template in the reaction and has in some studies been documented to represent 70-75% of the total yield [18]. Whole genome amplification is applied to amplify DNA in the PINS process and it would therefore be expected that these general challenges relating to bias in genome amplifications would also apply to PINS. As a procedure including multiple steps of WGA it would thus be expected that significant bias against the target DNA molecule should be observed. Hence a procedure such as PINS employing several steps of WGA would not have been considered as a method capable of enriching for a specific region of DNA in a mixed sample. Surprisingly, the challenge of TIP/bias is not seen when applying the PINS technique even though the initial concentration of the target DNA molecule is very low. The minimal negative TIP/bias observed in the PINS system is significantly lower than the overall gain obtained from the amplification process and the net result is therefore a substantial enrichment of the target DNA molecule with each cycle.

The method does not require a dilute initial DNA template, as high concentrations of DNA also can efficiently be subjected to PINS. In this case only a few fold amplification by the WGA method is needed.

EXAMPLES

The following examples illustrate why PINS is superior or complementary to other methods, such as shot-gun cloning and metagenomics, for the enrichment and/or isolation of a target DNA molecule. Employing traditional metagenomics, instead of PINS used in example 1, would require the sequencing of $2*10^6$ genomes with an average size of $3*10^9$ bases. Thus, a total of at least $6*10^{15}$ base pairs would be required in order to obtain the sequence of the HPV18. After two rounds of PINS the frequency of the HPV18 target was increased by a factor of 79 and therefore only $4.47*10^{13}$ base pairs would now need to be sequenced. Additional rounds of PINS could further decrease the required amount of sequencing.

Materials and General Methods

The following materials and methods were applied in the examples below:

Enzymes and reagents: If not stated otherwise enzymes were supplied by MBI Fermentas (Germany) and used according to the suppliers recommendations.

Amplification and detection methods: If not stated otherwise, the following procedures and conditions were employed for DNA fragment amplification by PCR; genome amplification by MDA; and extension of DNA fragment into flanking regions using RGW. The target DNA fragment was detected by 2% agarose gel electrophoresis.

PCR Amplification:

PCR reactions were: carried out in 20 µl reactions by mixing: nuclease free water (7 µl), 10 µl 2×SSO Advance Sybr TR-Mixture (BioRad), 5 µM fw-primer (1 µl ), 6 µM Re-primer (1 µl), with 1 µl DNA template. The composition of the 2×SSO Advance Sybr TR-Mixture is: dNTPs, Sso7d fusion polymerase, MgCl2, SYBR® Green I, and stabilizers.

PCR amplification conditions: were (15 sec/15 sec/15 sec)$_{\times 25}$ at temperatures (94° C./65.8° C./72° C.). The PCR reactions were performed in a BioRad Connect RT-PCR machine.

MDA amplification:

MDA was carried out according to the protocol described below:

Mix I: Denaturing & Re-annealing:
2.5 µl 2× Annealing buffer (33 mM Tris-acetate (pH 7.9 at 37° C.), 10 mM Mg-acetate, 66 mM K-acetate, 0.1 mg/mL BSA)
0.5 µl Water
1 pµl Exo-resistant random hexamer Primers (Thermo Scientific)
(1 µl DNA Template)*
Mix II—Amplification
7.5 µlWater
4 µl 2 mM dNTP
2 µl Phi29 buffer (Thermo Scientific)
1 µl Pyrophosphotase 0.01 U/µl (Thermo Scientific)
0.5 µl Phi29 polymerase (Thermo Scientific)
Protocol
1. Mix 1 was initially prepared without the addition of DNA template* and 4 µl mix 1 was added to each micro centrifuge tube. DNA template was then added to the mix by placing 1 µl inside the lid of the microcentrifuge tube. The tubes were centrifuged, and then transferred to ice immediately after centrifugation.
2. Mix 1 (from step 1) was then transferred from ice to 94° C. (pre-warmed PCR machine) and kept at 94° C. for three minutes and then transferred back to ice.
3. 15 µl from mix 2 was then added to mix 1 (from step 2).
4. The final mixture (mix1+mix2) was incubated at 30° C. for 16 hours (PCR machine). At the end of the incubation, the temperature of the final mixture was elevated to 65° C. for 10 minutes to inactivate the polymerase.

DNA quantification:

DNA was quantified using Quantus™ fluorometer (Promega) as described by the manufacturer. Gel electrophoresis: PCR results were evaluated on the basis of 2% agarose gel electrophoresis using BioRad SubCell Equipment. Gels were run at 80V in 1% agarose for 20-30 minutes. Visualization was done by casting Ethidium Bromide (0.5 µg/ml) into the gels.

MDA amplification was verified by loading 2 µl onto a 0.7% agarose gel. All MDA gels were run at 80V in 0.7% agarose for approximately 30 minutes.

The molecular marker on all agarose gels was Fermentas 1bk+ladder, with the band sizes (75, 200, 300, 400, 500, 1000, 2000, 3000, 4000, 5000, 7000, 10.000, 20.000).

Calculation of Probability

The probability of detecting a target DNA molecule in a sample was calculated using hypergeometric distribution, where the population is the original sample volume of liquid in which the target is either present (positive) or not present and the test sample is the volume of liquid withdrawn from the original sample. Because the nucleic acid molecules only contribute to a minor part of the volume, both the population volume and test sample volumes are multiplied by 1000 in the calculations.

For a 100 μl sample, the population size is 100000. If 100 μl sample contains four target DNA molecules, the probability of detecting a target DNA molecule in a diluted sample containing 3.5 μl (test sample=3500) of the original 100 μl sample is:

$P=1-\text{Hypgeom.dist}(0;3500;4;100000)=0.133$

If 10 replicate dilution test samples of each 3.5 μl are analyzed from the same original sample, the probability of detecting the target DNA molecule in at least one of the replicate dilution samples is:

$P=1-\text{Hypgeom.dist}(0;35000;4;100000)=0.821$

The equation for the hypergeometric distribution is:

$$P(X=x) = h(\pi; n, M, N) = \frac{\binom{M}{x}\binom{N-M}{n-x}}{\binom{N}{n}}$$

where:
x=number of positives in the (diluted) test sample
n=the volume of (diluted) test sample*1000
M=number of target DNA molecules in the original sample (population)
N=the volume of the original sample (population)*1000

Example 1

Method of Enrichment of a Polynucleotide Encoding HPV-18 Virus from a Mixed Sample of Human DNA 1.0 Creating the Mixture for Enrichment A mixed polynucleotide sample was prepared from reference DNA that was spiked with DNA derived from HeLa cells. The HeLa DNA was obtained from New England Biolabs (100 μg/ml) as a purified DNA sample. The reference DNA was extracted from cells derived from a human volunteer. The target DNA molecule in the HeLa DNA was efficiently amplified by the selected target PCR primers [SEQ ID NO: 1 and SEQ ID NO: 2], whereas the human reference DNA did not yield an amplification product with this primer pair. Both types of DNA were amplified separately using the MDA protocol prior to setting up the mixture. Following the MDA amplification, the quantity of target DNA copies in MDA amplified HeLa DNA was determined to be 71750 copies/μl using most probable number (MPN) calculation on triplicate 10-fold dilutions of HeLa DNA. The target DNA was diluted by a factor of 1:2.500.000 in undiluted MDA amplified reference DNA (employing serial dilution) to create the final spiked mixture containing 0.029 targets copies/μl and having a total DNA concentration of 0.187 μg/μl. Thus, the initial quantity of target DNA copies in the initial mixed polynucleotide sample was calculated to be: (0.029 target copies/μl):(0.187 μg/μl)=0.153 target copies/μg DNA. The total volume of mixed DNA sample was 45 μl.

The probability of detecting the target DNA molecule in 3.5 μl mixed polynucleotide sample is 0.078 (1-hypgeo(0; 3500;1;45000)); i.e. less than 0.75. 3.5 μl is the volume of sample used in the first round of PINS.

1.1 Defining the primers for selection of the target DNA molecule encoding HPV18:

DNA sequence from HPV18 was obtained from GenBank (GQ180790), and the following 2 primers were designed manually to target a DNA fragment of 96 bp in the HPV18 genome (GenBank Acc. No: GQ180790):

```
Fw primer:
                                            [SEQ ID NO: 1]
GTTTAGTGTGGGCCTGTGC Rev primer:
                                            [SEQ ID NO: 2]
GGCATGGGAACTTTCAGTGT
```

1.2 Initial Mixture—Below Limit of Detection:

PCR analysis was carried out to verify that the number of target DNA molecules was below the limit of PCR detection in the initial polynucleotide mixture. Nine polynucleotide mixture samples (each with 1 μl of initial mixture) were used as DNA template for PCR amplification with the primer pair [SEQ ID NO: 1 and 2], but no PCR products of the expected 96 bp were found in any of the samples. An agarose gel showing the individual negative PCR samples from the initial mixture can be found in FIG. 1.

1.3 First Round of PINS

Ten individual 3.5 μl samples of the mixed polynucleotide sample, prepared in step 1, were chosen for MDA amplification in a volume of 20 μl, as described above, where the probability of detecting the target DNA molecule in 3.5 μl mixed polynucleotide sample prior to amplification is 0.078 (1-hypgeo(0;3500;1;45000)); i.e. less than 0.75. 1 μl triplicate aliquots of each MDA amplified sample (#1-#10) were screened for the presence of the target DNA molecule by PCR amplification, as described above using the target-specific PCR primer pair in 1.1., followed by agarose gel electrophoresis to visualize PCR products (FIG. 2). Because ten replicate samples were analysed, the probability of detecting the target DNA molecule in at least one of the ten replicate dilution samples was 0.778 (1-hypgeo(0;35000;1; 45000)) i.e. higher than 0.75. #10 was the only sample found to result in positive PCR products of the correct size in all three replicates. Ten additional samples (each with 1 μl template) from #10 were analysed by PCR using identical conditions, and 5 (out of 10) resulted in a correct PCR product. By combining the results from the first screening 3 (of 3) and the following screening, where 5 (of 10) were positive, a total of 8 (of 13) were observed as positive, all originating from #10. The concentration of total DNA in sample #10 was quantified to be 0.222 μg/μl. An agarose gel showing 10 PCR products from the second screening can be found in FIG. 2.

The abundance of the target DNA molecule after MDA amplification was calculated to: (8/13 target DNA copies/ μl):(0.208 μg/μl)=2.96 target DNA copies/μg. Consequently, the increase in frequency obtained by PINS in the first round of amplification is: (2.96 targets/μg): (0.153 targets/μg)=19.36 fold.

Re-Amplification of #10

To generate sufficient amount of template prior to progressing to the 2nd round of PINS, 3.5 μl template from #10 was amplified by using a 50 μl MDA reaction mixture. The result of re-amplification of #10 was verified by analysing ten 1 μl aliquots by PCR where, in 6 of 10 PCR reactions, the target DNA molecule was detected (0.60 target DNA copies/µl). This result corresponds well to the initial frequency of the target DNA molecule in #10 which was 8/13 (0.62). By dividing with frequency of the target copies/µl sample by the total DNA concentration, the relative abundance of the target DNA molecule is calculated to be: (0.6 targets/µl):(0.222 µg/µl)=2.70 targets/µg.

Surprisingly, an amplification bias had apparently only occurred to a limited degree during re-amplification. An agarose gel showing the ten PCR reactions products from the re-amplification can be found in FIG. 3.

1.4 Second Round of PINS

Ten 1 µl aliquots of sample the re-amplification of #10, derived from $1^{st}$ round of PINS, were diluted 20 fold in the MDA reaction mixture thereby diluting the target DNA molecule to a frequency of 0.03 target DNA molecules/µl. The probability of detecting the target DNA molecule (HPV18) in a 1 µl aliquot of the diluted sample was 1−hypgeo(0;1000;30;50000)=0.455 i.e. below 0.75. Each aliquot was amplified using the MDA protocol described above. Out of the ten MDA reactions, the target DNA molecule was detected in two reactions samples, #8 and #10, where 3 (of 3) replicated PCR reactions were positive for the target. The probability of detecting the target in at least one of the ten replicate samples was 1−hypgeo(0;10000;30; 50000)=0.9988 i.e. above 0.75.

Samples #8 and #10 were pooled in one sample and diluted $2*10^{-1}$ (5-fold). Analysis of 1 µl aliquots of this dilution by PCR, detected the target DNA molecule in 5 (of 10) PCR reactions, as seen in the gel in (FIG. 4). Since the pooled sample was diluted $2*10^{-1}$ (5-fold), the quantity of targets is calculated to be: 5 targets /10 µl test sample volume*5=2.5 targets/µl. Since the total DNA content of the pooled sample was measured to 0.207 µg/µl, the frequency of the target DNA molecule is calculated to 2.5 targets/µl divided by 0.207 µg total DNA/µl; which corresponds to 12.08 targets/µg DNA.

An overview of the protocol followed through the two rounds of PINS is set out in FIG. 5.

1.5 Calculated Enrichment for Target Molecule DNA by Two Rounds of PINS

By calculating from the initial mixture (0.153 targets/µg) to the final sample (12.08 targets/µg) a total gain of 79.05 has been reached after two consecutive rounds of PINS amplification.

The abundance of the HPV18 target before first round of PINS was $1/1.97*10^6$ HPV18 positive genome equivalent/ total genome equivalents. The corresponding abundance after first and second round of PINS was $1.02*10^5$ and $2.49*10^4$, respectively. This enrichment was achieved using 21 tests and the requirement for required number of traditional tests such as sequencing was decreased by a factor of 79 as can be seen in Table 1.

Example 2

The use of PINS to facilitate the sequencing of a target DNA molecule present in a mixed polynucleotide sample, where the amount of target DNA is below the limit of detection by PCR is demonstrated in this example. The selected target DNA molecule was a polynucleotide located within HPV18 genome. The amount of this target DNA molecule in the mixed sample corresponded to 0.0286 copies/µl. The mixed sample was prepared as described in Example 1. Using standard PCR protocols, the amount of template solution added to a PCR reaction is normally 1 µl, and the minimum target DNA concentration required for its positive detection by PCR is 1 copy/µl. Accordingly, the amount of target DNA molecule in the mixed polynucleotide sample was approximately 35 times below that required for PCR amplification and subsequent sequencing. The example demonstrates how PINS can be used to determine the sequence of target DNA in a mixed sample, which has otherwise been unattainable by known standard PCR based procedures.

2.1 The target HPV18 DNA Molecule in the Mixed Polynucleotide Sample is Not Detectable by PCR In order to verify that the number of copies of target DNA molecule per µl of the mixed polynucleotide sample (corresponding the mixed polynucleotide sample of Example 1, prior to MDA amplification) was below the detection limit for PCR, a series of ten duplicate samples were PCR amplified (according to protocol given in Material and General Methods), with the modification of using 50 cycles and using the optimized amplification parameters: 94° C./65.8°/72° C., where each temperature was maintained for 15 seconds. HPV-specific primers used during amplification were:

```
HPV-264f:
                                          [SEQ ID NO: 3]
5'-GTGGTGTATAGAGACAGTATACC-3'

HPV-911f:
                                          [SEQ ID NO: 4]
5'-CCTTCTGGATCAGCCATTGT
```

Positive amplification of the target DNA molecule in the HPV18 genome would generate a PCR product of 667 bp (Boxed in FIG. 6). As expected, due to the low abundance none (of ten) reactions resulted in amplification of the correct size, verifying the low quantity of target DNA molecule in the mixed polynucleotide sample (FIG. 6).

2.2 PINS Facilitates Enrichment of the Target HPV18 DNA Molecule in the Mixed Polynucleotide Sample to Allow its PCR Detection The initial copy number of the target DNA molecule in the mixed polynucleotide sample (0.0286 target copies/µl) was increased to a final quantity of 2.5 target copies/µl by the implementation of PINS as described in Example 1. The MDA amplification products, generated by performing $1^{st}$ round PINS on the initial mixed polynucleotide sample, were analysed by PCR as described above using 1 µl of the MDA amplified sample. A PCR product of the expected size (667 bp) was obtained as shown in FIG. 7. Low levels of non-specific amplification of the initial mixed polynucleotide sample generated a low background detectable as a smear in lane #2 of FIG. 7. The detectable product of ~667 bp in lane #2 was isolated by gel-out (GeneJet Gel-out kit, Thermo Fischer Scientific) and PCR re-amplified to increase the amount of the target DNA molecule to allow subsequence sequencing (lane #A, FIG. 8).

2.3 Verification of the Target HPV18 DNA Molecule Obtained by PINS

Figure 9:
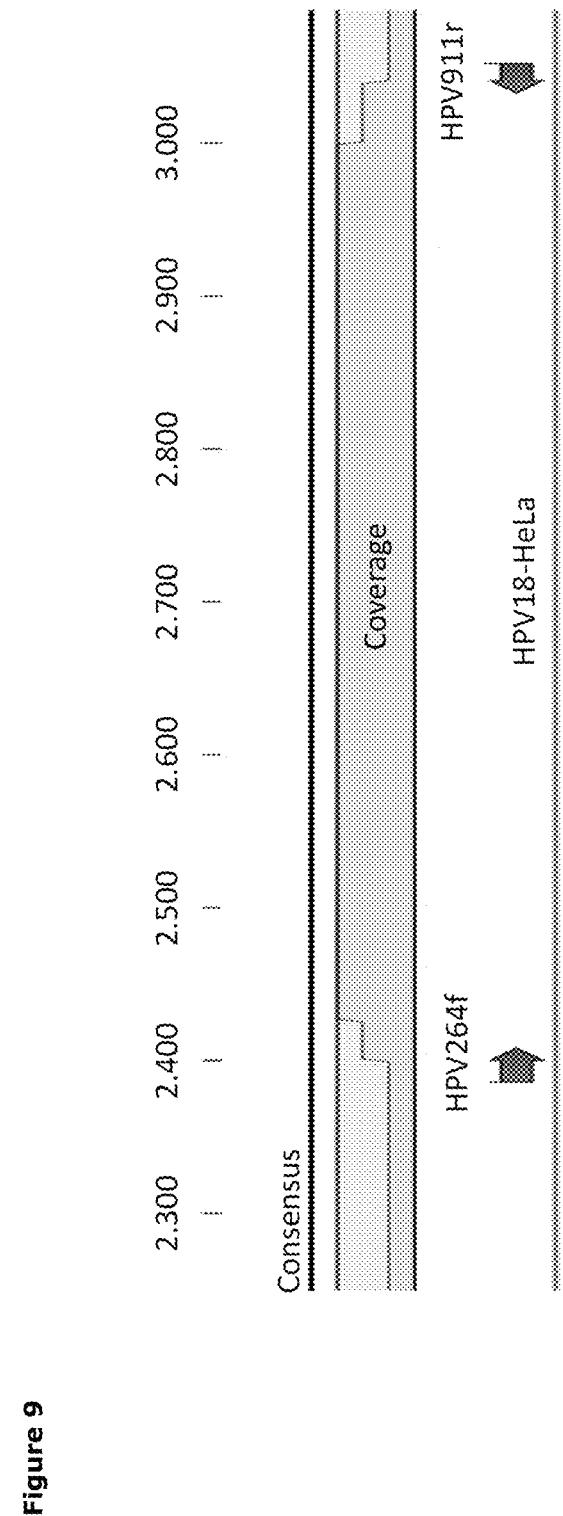

The purified product isolated from lane #A (FIG. 8) was sequenced forward and reverse using both primers [SEQ ID NO: 3 and 4]. The retrieved sequences were aligned to the sequence of HPV18 (HPU89349) resulting in a perfect alignment with zero mismatches (FIG. 9). The example confirms the efficacy of PINS for enriching for rare sequences to a level where their sequence can be determined.

Example 3

Method of Isolating a Nucleotide Fragment Encoding an Endoglucanase Enzyme from a Soil Sample 3.1 Defining the Primers for Selection of the Target DNA Molecule Encoding an Endoglucanase:

Multiple microbial genes encoding endoglucanases and putative endoglucanases are retrieved from GenBank and their nucleotide sequences are aligned using ClustalW alignment for multiple sequences[9]. From the alignment, regions of conserved nucleic acid sequence are identified and a set of primers is designed to target a DNA molecule having one of these conserved DNA sequences. Primers and partial alignments of the sequences of retrieved genes encoding endoglucanase are shown in FIG. 10.

The selected primers are estimated to result in a PCR amplification product of 481 bp. However, as the origin and sequence of the templates in a natural sample are unknown, the sizes of PCR products may deviate from the expected size.

3.2 Extraction of the DNA from the Soil Sample:

Samples (8) of forest soils are collected as a source of diverse soil micro-organisms. DNA from the 8 different samples are extracted using Bead Beating, as described by Kvist et. al [10]. Each extraction is amplified using MDA Repli-g Mini kit, using MDA amplification conditions as defined above (Materials and general methods). The quality of the amplified DNA is verified by visualization on 0.7% agarose gels.

3.3 Determining of the Presence and Abundance of the Target DNA Molecule:

The initial PCR analysis is carried out to evaluate if the target DNA sequence could be observed using the selected primers [SEQ ID NO: 5 and 6] using the selected PCR conditions: 94° C. (30 sec)+60° C. (30 sec)+72° C. (30 sec) and 30 cycles is carried out.

One (out of eight) MDA amplified sample results in a positive PCR amplification, whereas the remaining 7 show no sign of amplification. The PCR product is evaluated to have approximately the correct predicted size on an agarose gel. By performing Real Time PCR (RT-PCR), the abundance of the target DNA molecule (encoding a putative endoglucanase) is determined using primers [SEQ ID NO: 5 and 6] and compared to the abundance of 16S rRNA genes using primers [SEQ ID NO: 7 and 8] (where the 16S rRNA gene is used as a measure of total bacterial DNA abundance). It is found that 16S rRNA genes are approximately 550.000 higher in quantity compared to the putative endoglucanase. Quantification reveals that 16S rRNA genes are present in 9.4E6 copies, whereas endoglucanase was detected only in 17 copies. Thus, a dilution of $10^{-2}$ was required to generate samples (N), as each aliquot sample would then averagely contain 0.17 templates.

3.4 Application of the PINS Procedure to Enrich and Isolate the Targeted DNA Molecule and Its Flanking Regions:

DNA samples found to contain the targeted DNA molecule, are subjected to PINS as follows:

3.4.1: $1^{st}$ Round PINS

Based on the above detected quantification, a dilution series is created using a dilution factor (D) of 1:10, aimed at then setting up multiple replicate dilutions of (N), $10^{-2}$. Twenty identical samples of $10^{-2}$ dilution are prepared and subjected to genomic amplification, using Repli-g Mini kit (Qiagen). Each amplified sample is individually analysed using the PCR primers [SEQ ID NO: 5 and 6] and the RT-PCR conditions described above in 1.3. Three out of 20 samples results in positive PCR amplification, with a DNA product of the predicted size. The associated PINS analysis output data are listed below.

PINS data #1

PINS quant no: 24.3

Dilution factor: 10

Next dilution: $10^{-3}$

Samples in next repetition: 20

3.4.2: $2^{nd}$ Round PINS

Based on the PINS-software analysis from the previous round (PINS#1), a total of at least 20 replicate samples are estimated for next round of replication. Thus, 20 samples of dilution $10^{-3}$ are prepared (i.e. a 10 fold dilution (D) increase over the previous total dilution of the sample (Dt)), and each of the individual samples are amplified using Repli-g MDA kit. Each sample is subsequently analyzed by RT-PCR using primers [SEQ ID NO: 5 and 6] which shows that one (out of 20) sample yielded a DNA product of the predicted size. This sample is selected for further progress. PINS analysis output data are listed below.

PINS data PINS#2

PINS quant no: 230

Dilution factor: 9.6

Next dilution: $10^{-4}$

Samples in next repetition: 20

3.4.3: $3^{rd}$ Round PINS

Based on the PINS#2 calculated values, it is estimated that at least 20 samples are again required for the next round of enrichment. The dilution proposed by the software is $10^{-4}$ and 20 samples are prepared. The 20 samples are amplified using the Repli-g Mini Kit, and are subsequently subjected to RT-PCR amplification using primers [SEQ ID NO: 5 and 6], where four samples yields a DNA product of the predicted size. These four samples are pooled and used for next round of repetition. PINS analysis output data are listed below.

PINS data PINS#3

PINS quant no: 2840

Dilution factor: 12

Next dilution: $8.4*10^{-6}$

Samples in next repetition: 25

3.4.4: $4^{th}$ Round PINS

Based on the PINS#3 calculated values, a total of 25 samples are now created having the dilution $8.4*10^{-6}$. Each of the individual replicated dilution samples are amplified using Repli-g Mini Kit. RT-PCR analysis using primers [SEQ ID NO: 5 and 6] shows that two samples yield a DNA product of the predicted size. PINS analysis output data are listed below.

PINS data PINS#4

PINS quant no: 27200

Dilution factor: 12

Next dilution: $8.8*10^{-7}$

Samples in next repetition: 25

3.4.5: $5^{th}$ round PINS

Based on the PINS#4 calculated values, a total of 25 samples are now created in dilution $8.8 \cdot 10^{-7}$. And, each of the individual samples are amplified using Repli-g Mini Kit. RT-PCR analysis using primers [SEQ ID NO: 6 and 6] shows that two samples yield a DNA product of the predicted size.

PINS software results are listed below.
PINS data PINS#5
PINS quant no: 365000

The two positive samples from this round of analysis are pooled into one sample, and RT-PCR is carried out on the targeted gene using primers [SEQ ID NO: 5 and 6] and 16S rRNA genes using primers [SEQ ID NO: 7 and 8] in the same sample. Levels of total DNA (as measured by rRNA genes) following the 5 rounds of MDA amplification, have not changed markedly compared to the initial observations but the ratio of target DNA to total DNA is now calculated to be 365000/9200000=approximately 1/25. Previous studies have shown that a ratio 1:100 is sufficient to obtain genome data by RGW. Each of the amplification primers are combined with the linker ligation primers of the RGW.

3.4.6: Sequencing of the Target DNA Molecule Enriched by PINS

The 5 cycles of PINS serves to enhance the presence of the targeted DNA molecule to such extent that the entire gene and a potential operon comprising the targeted DNA molecule, placed can be sequenced by traditional sequencing methods. Consequently, the RGW technique [7] is implemented in which 3 random libraries of the DNA sample, enriched with target DNA molecule are generated by preparing 3 restriction digests (EcoRI, HindIll and BglII/MboI) and then annealing the digests each with RGW primers comprising compatible 5' overhangs, for example primer pair [SEQ ID NO: 5] and [SEQ ID NO: 6] to form an oligo-cassette. The target DNA molecule specific primers used for screening [SEQ ID NO: 5 and 6] are used in combination with the RGW primer [SEQ ID NO: 5] in a PCR amplification to generate larger PCR products that span the target DNA molecule and its flanking regions.

Initially, two DNA sequences are generated using the procedure, and additional design of primers based on the acquired sequence results in a complete assembly of one ORF constituted of a 3996 bp gene (FIG. 11). The gene has an ATG start code placed 196 bp up-stream of the EndoGlu-fw (5') end. A ShineDalgarno and associated −10 & −35 boxes are be located in the 5'direction of the ATG start code. Moreover, no apparent linkage to genes in 3' direction was found, illustrating that the gene is probably not a part of a larger operon.

Example 4

Use of PINS to Link Multiple Genetic Elements of Common Genomic Origin

This example illustrates the use of PINS to detect the presence of the mecA gene in a mixed sample (e.g. taken from a patient) and to determine whether the gene originates from the genome of *Staphylococci* present in the sample. This analysis relies on the use of PINS to monitor the simultaneous co-amplification of a *Staphylococcus* gene located approximately 13000 base pairs up-stream of the mecA gene. The experiment is designed to use the high fidelity of phi29 polymerase for multiple displacement amplification (MDA), allowing genome fragments up to +70000 bp to be generated during amplification. If, after implementing PINS, the levels of PCR products generated using primers specific for mecA gene and for *Staphylococcus aureus* (SA) reach comparable quantities, this indicates that the PCR products originate from the same genome, namely MRSA, as they have been co-amplified within the range of MDA. Assembly of sequenced PCR products after PINS is used to confirm that the mecA originated from a *Staphylococcus* genome.

4.1 Primer Design

Multiple sequences of microbial genes coding for mecA are retrieved from the GenBank database and these sequences are aligned using ClustalW for multiple sequence

| Primer nucleotide sequence | Description |
|---|---|
| >WalkID: GCG CTG CAG GCA TGC GAG CTC [SEQ ID NO: 9] | Used as PCR primer together with specific primer |
| >WALKOL_EcoRI_I: GCGCTGCAGGCATGCGAGCTCCCAAGCTTGATCG [SEQ ID NO: 10] >WALKOL_EcoRI_II: AATTCGATCAAGCTTGGGAGCTCGCATGCCTGCAGCGC [SEQ ID NO: 11] | Linkers used for EcoRI digested DNA |
| >WALKOL_HindIII: GCGCTGCAGGCATGCGAGCTCCCA [SEQ ID NO: 12] >WALKOL_HindIII_II: AGCTTGGGAGCTCGCATGCCTGCAGCGC [SEQ ID NO: 13] | Linkers used for HindIII digested DNA |
| >WALKOL_BglII: GATCTGGGAGCTCGCATGCCTGCAGCGC [SEQ ID NO: 14] >WALKOL_BglII_II: GCGCTGCAGGCATGCGAGCTCCCAAGCTTGATCG [SEQ ID NO: 15] | Linkers used for BglII/MboI digested DNA | alignment [9]. Regions of the alignment with 100% sequence identity are located and used for primer design. The resulting primers targeting mecA are:

```
MR-fw:
                                      [SEQ ID NO: 16]
5'-CAAACTACGGTAACATTGATCGCAAC-3'

MR-Re:
                                      [SEQ ID NO: 17]
5'-CAATATGTATGCTTTGGTCTTTCTGC-3',
``` and which are predicted to generate a 126 bp PCR product.

Strain specific primers used to target *Staphylococcus aureus* are designed approximately 13,000 bp 5' up-stream from the SCCmec integration site of resistance (OrfX) [14]. Primer sequences are:

```
SA-fw:
                                      [SEQ ID NO: 18]
5'-CGTGAAGAAACAGAACGAATGATTC-3',

SA-Re:
                                      [SEQ ID NO: 19]
5'-GCCTCTAGAATATTTCATCGCATTTG-3',
``` and which are predicted to generate a 267 bp PCR product.

4.2 Primary Biological Sample Collection and DNA Extraction and Quantification

A sample suspected to contain MRSA is subjected to PINS analysis. The sample is collected from a patient by the use of a "cotton-stick-swab". Total DNA is extracted from the swab using A&A Biotechnology (Poland) DNA Swab extraction kit.

The extracted DNA is used as template for a 10-fold serial dilution. Each of the diluted tubes are directly analyzed by Real-Time (RT) PCR using 1 µl template in a 25 µl RT-reaction mix with each of the two sets of primers MR (MR-fw and MR-Re) and SA (SA-fw and SA-re).

From the RT-PCR analysis targeted at MR (mecA), the Ct value is measured and converted to absolute numbers/copies by comparison to internal standards running in parallel samples in the same cycle program. The quantity of MR (mecA) is calculated to be $1.70*10^2$ whereas SA (*Staphylococcus aureus*) is calculated to be present in a quantity of $1.34*10^3$. From the RT analysis, it is apparent, that the sample contains more *Staphylococcus* targets than mecA targets. The ratio of the two products is close to 1/8 (MR/SA).

4.3 Application of the PINS Procedure to Enrich and for Target DNA Molecules Diagnostic of mecA and *Staphylococcus*

4.3.1: 1$^{st}$ Round PINS #1

Based on the detected levels of target DNA molecules in the initial sample, 10 replicates of sample N (dilution $1.7*10^{-3}$) are prepared. By applying Repli-g Ultra-fast to each of the ten replicated samples and by subsequently performing RT-PCR analysis to detect the MR target DNA molecule, it is found that one sample from the 10 samples ("Sample E") yields a large amount of MR-PCR product, whereas the 9 other samples does not comprise detectable levels of MR PCR product. In this MR positive sample, RT-PCR quantification shows that the abundance of MR-PCR product is $1.27*10^3$ and the abundance of the SA-PCR product in sample $1.31*10^3$. The ratio has now shifted towards comparable levels of the two target DNA molecules, from having an initial ratio of approximately 1:8, up to a ratio that is closer to 1:1.

4.3.2: 2$^{nd}$ Round PINS #2

Based on the positive "E" sample, having dilution $1.27*10^{-3}$ (2.3.1) another dilution series is set up and, again, 10 replicated samples of N (dilution $1.27*10^{-4}$) are prepared. Each of the samples are amplified using Repli-g Ultra-fast MDA kit. From the RT-PCR of the analysis, it is apparent, that MR can be detected in 9 out of 10 samples, and that abundance of MR in the positive samples is $1.32*10^4$. Comparable analysis reveals, that the level of the SA-PCR product has not increased, as the abundance of SA remains identical: $1.31*10^4$. The ratio of the two products are, again, very close to 1:1. Having employed PINS to obtain an additional amplification factor of ×10 without obtaining any noticeable change in target abundance, we conclude that the quantity cannot be further increased, indicating the presence of a (close to) pure sample. Additional rounds of PINS will, thus, not result in a higher level of purification. Thus, the next step is to sequence the amplified template to evaluate the identity of the resistance gene mecA and the adjacent genes, and to verify the presence of MRSA rather than MR and SA as independent DNA molecules located in the same sample.

4.3.3: Sequencing mecA and Adjacent Genes in the MR Target DNA Molecule

Primers designed to target known MRSA (GenBank, NCBI,) are used to generate overlapping PCR products used for sequencing and assembly. 24 PCR products of various lengths are generated and two continuous sequences of 2475 bp. and 19186 bp. are produced by PCR, sequencing, and assembly. An additional 789 bp are obtained by RGW [7] and sufficient overlap is established to combine the two assemblies into one large assembly of 22450 bp. Nucleotide BLAST [11] shows close to identical match (>99.9%) to multiple MRSA strains in the database.

SUMMARY

It was evaluated, that the abundance of MR had increased by a factor of 8 by the first round of PINS. By performing analysis on the non-targeted background, it is apparent that the ratio between MR and SA was clearly biased during the first run (PINS #1), whereas this ratio was maintained in the following round of amplification (PINS #2). Thus, it is concluded, that both target DNA molecules originate from the same DNA fragment, since the non-target SA is present in equal quantity even though only the MR target DNA molecule has been used during the rounds of PINS selection. It is apparent from the analysis, that although non-resistant *Staphylococci* presumably also are present in the initial mixture, it can be concluded that the MR resistance originated from a *Staphylococcus aureus* and not from other mecA containing bacteria such as coagulase-negative *Staphylococci* [12]. Although MR can be present in non-*Staphylococcal* bacterial strains, it was evidently amplified together with SA, due to the co-amplification of both targeted DNA molecules during MDA amplification. Thus, although the primed sequences are separated by 13000 kb in the genome, it is possible to assign both properties to the same fraction of the genome, sufficient to diagnose the presence of MRSA. In addition, sequencing verifies this observation, and it was evident that the DNA was close to identical (+99.9%) to known MRSA genome sequences.

REFERENCES

1. Maurin, M., *Real-time PCR as a diagnostic tool for bacterial diseases*. Expert Rev Mol Diagn, 2012. 12(7): p. 731-54.

2. Shendure, J. and H. Ji, *Next-generation DNA sequencing.* Nat Biotechnol, 2008. 26(10): p. 1135-45.
3. Torsvik, V., J. Goksoyr, and F. L. Daae, *High diversity in DNA of soil bacteria.* Appl Environ. Microbiol, 1990. 56(3): p. 782-787.
4. Lasken, R. S. and S. Huges, *Multiple displacement amplification of genomic DNA*, in *Whole Genome Amplification*, S. Huges, Editor 2005, Scion Publishing Ltd. 2005: Oxfordshire. p. 99-118.
5. Sambrook, J. and D. W. Russell, *Molecular Cloning a laboratory manual* 2001: Cold Spring Harbor Laboratory Press.
6. Raghunathan, A., et al., *Genomic DNA amplification from a single bacterium.* Applied and Environmental Microbiology, 2005. 71(6): p. 3342-3347.
7. Kilstrup, M. and K. N. Kristiansen, *Rapid genome walking: a simplified oligo-cassette mediated polymerase chain reaction using a single genome-specific primer.* Nucleic Acids Res, 2000. 28(11): p. e55.
8. Liu, L., et al., *Comparison of next-generation sequencing systems.* J Biomed Biotechnol, 2012. 2012: p. 251364.
9. Chenna, R., et al., *Multiple sequence alignment with the Clustal series of programs.* Nucleic Acids Res., 2003. 31(13): p. 3497-3500.
10. Kvist, T., et al., *Diversity of thermophilic and non-thermophilic crenarchaeota at 80 degrees C.* FEMS Microbiol. Lett., 2005. 244(1): p. 61-68.
11. Altschul, S. F., et al., *Basic local alignment search tool.* J. Mol. Biol., 1990. 215(3): p. 403-410.
12. Huletsky, A., et al., *Identification of methicillin-resistant Staphylococcus aureus carriage in less than 1 hour during a hospital surveillance program.* Clin Infect Dis, 2005. 40(7): p. 976-81.

The invention claimed is:

1. An in vitro method for enriching for a pre-defined target DNA molecule containing a known unique sequence of consecutive nucleotides from a mixed polynucleotide sample comprising the steps of:
   a) providing a mixed polynucleotide sample containing said target DNA molecule and non-target DNA molecules, wherein said target DNA molecule comprises a known unique sequence of at least 10 consecutive nucleotides which is distinguishable from sequences in the non-target DNA molecules,
   b) serially diluting said mixed polynucleotide sample until the probability that the target DNA molecule is present in a diluted sample of mixed polynucleotides is less than 0.75,
   c) producing a sufficient number of replicates of the diluted sample of mixed polynucleotides until the probability that the target DNA molecule is present in at least one of the replicate dilution samples is at least 0.75;
   d) amplifying all DNA in said replicate diluted samples to increase the abundance of the DNA in each sample;
   wherein the frequency of said target DNA molecule in said at least one replicate dilution sample is increased compared to the mixed polynucleotide sample in step (a); and
   wherein the probability in (b) and (c) is calculated using a hypergeometric distribution according to the following equation:

$$P(X = x) = h(x; n, M, N) = \frac{\binom{M}{x}\binom{N-M}{n-x}}{\binom{N}{n}}$$

where x is the number of target DNA molecules in the diluted sample, n is the volume of the diluted sample multiplied by 1,000, M is the number of target DNA molecules in the mixed polynucleotide sample, and N is the volume of the mixed polynucleotide sample multiplied by 1,000.

2. The method according to claim 1, further comprising: (e) serially diluting at least one replicate dilution sample amplified in step (d) until the probability that the target DNA molecule is present in the at least one replicate dilution sample is less than 0.75, and repeating steps (c) through (d) or (e) at least once.

3. The method according to claim 1, wherein the frequency of said target DNA molecule relative to non-target DNA in a mixed polynucleotide sample of step a) is between $10^{-2}$ and $10^{-7}$.

4. The method according to claim 1, wherein the serial dilutions of said mixed polynucleotide sample in step (b) are amplified to increase the abundance of the DNA in each sample, followed by a step of detecting the presence or absence of said target DNA molecule in each amplified sample, and thereby determining the number of serial dilutions required to obtain a diluted sample, wherein the probability of detecting said target DNA molecule is less than 0.75.

5. The method according to claim 1, wherein the DNA is amplified in step (d) by degenerate primed PCR, linker ligation PCR, Degenerate Oligonucleotide Primed (DOP) PCR, or Multiple Displacement Amplification.

6. The method according to claim 1, further comprising performing nucleic acid sequence analysis on said target DNA molecule to determine at least part of the nucleotide sequence of the target DNA molecule.

7. The method according to claim 1, wherein the presence of said unique sequence of at least 10 consecutive nucleotides in said target DNA molecule is detected by PCR.

8. The method according to claim 1, wherein the presence of said unique sequence of at least 10 consecutive nucleotides in said target DNA molecule is detected by hybridization to said target DNA molecule.

9. The method according to claim 1, wherein said target DNA molecule comprises at least two unique sequences of at least 10 consecutive nucleotides, and wherein said target DNA molecule comprises 50 to 100,000 nucleic acid basepairs.

10. The method according to claim 2, wherein the total dilution of the diluted sample of step (e) is increased by a factor 2 to 20 for each repetition of steps (c) through (d).

11. The method according to claim 1, wherein the number of replicate dilution samples prepared in step (c) is 2 to 500.

12. The method according to claim 1, wherein the target DNA molecule is derived from the genome of a cell.

13. The method according to claim 12, wherein the cell is selected from a bacterial cell, a fungal cell, and a mammalian cell.

14. The method according to claim 1, wherein the target DNA molecule is derived from a viral genome or a mammalian genome or a combination thereof.

15. The method of claim 1, wherein the probability that said target DNA molecule is present in the diluted sample of mixed polynucleotides is less than 0.50.

16. The method of claim 1, wherein the probability that said target DNA molecule is present in the diluted sample of mixed polynucleotides is less than 0.25.

17. The method of claim 1, wherein the probability said target DNA molecule is present in at least one of the replicate dilution samples is 0.80 to 0.95.

18. The method of claim 3, wherein the frequency of said target DNA molecule relative to non-target DNA in a mixed polynucleotide sample of step a) is between $10^{-4}$ and $10^{-7}$.

19. The method of claim 1, wherein said target DNA molecule comprises 150 to 3,000 nucleic acid basepairs.

20. The method of claim 1, wherein said target DNA molecule comprises 150 to 1500 nucleic acid basepairs.

* * * * *

```
                              SEQUENCE LISTING

<160> NUMBER OF SEQ ID NOS: 19

<210> SEQ ID NO 1
   <211> LENGTH: 19
   <212> TYPE: DNA
   <213> ORGANISM: Human papillomavirus type 18
   <220> FEATURE:
   <221> NAME/KEY: primer_bind
   <222> LOCATION: (1)..(19)
   <223> OTHER INFORMATION: HPV18 fw primer

<400> SEQUENCE: 1
gtttagtgtg ggcctgtgc                                                 19

<210> SEQ ID NO 2
   <211> LENGTH: 20
   <212> TYPE: DNA
   <213> ORGANISM: Human papillomavirus type 18
   <220> FEATURE:
   <221> NAME/KEY: primer_bind
   <222> LOCATION: (1)..(20)
   <223> OTHER INFORMATION: HPV18 Rev primer

<400> SEQUENCE: 2
ggcatgggaa ctttcagtgt                                                20

<210> SEQ ID NO 3
   <211> LENGTH: 23
   <212> TYPE: DNA
   <213> ORGANISM: Human papillomavirus type 18
   <220> FEATURE:
   <221> NAME/KEY: primer_bind
   <222> LOCATION: (1)..(23)
   <223> OTHER INFORMATION: HPV-264f primer

<400> SEQUENCE: 3
gtggtgtata gagacagtat acc                                            23

<210> SEQ ID NO 4
   <211> LENGTH: 20
   <212> TYPE: DNA
   <213> ORGANISM: Human papillomavirus type 18
   <220> FEATURE:
   <221> NAME/KEY: primer_bind
   <222> LOCATION: (1)..(20)
   <223> OTHER INFORMATION: HPV-911f primer

<400> SEQUENCE: 4
ccttctggat cagccattgt                                                20
```

```
<210> SEQ ID NO 5
<211> LENGTH: 22
<212> TYPE: DNA
<213> ORGANISM: Bacillus acidopullulyticus
<220> FEATURE:
<221> NAME/KEY: primer_bind
<222> LOCATION: (1)..(22)
<223> OTHER INFORMATION: EndoGlu - Fw primer

<400> SEQUENCE: 5
gcacattgct ggtacagaga ta                                              22

<210> SEQ ID NO 6
<211> LENGTH: 22
<212> TYPE: DNA
<213> ORGANISM: Bacillus acidopullulyticus
<220> FEATURE:
<221> NAME/KEY: primer_bind
<222> LOCATION: (1)..(22)
<223> OTHER INFORMATION: EndoGlu Re primer

<400> SEQUENCE: 6
gatctgcttc cattatgctc tg                                              22

<210> SEQ ID NO 7
<211> LENGTH: 19
<212> TYPE: DNA
<213> ORGANISM: Artificial Sequence
<220> FEATURE:
<221> NAME/KEY: primer_bind
<222> LOCATION: (1)..(19)
<223> OTHER INFORMATION: Synthesized 16S rRNA forward primer

<400> SEQUENCE: 7
gagtttgatc ctggctcag                                                  19

<210> SEQ ID NO 8
<211> LENGTH: 18
<212> TYPE: DNA
<213> ORGANISM: Artificial Sequence
<220> FEATURE:
<221> NAME/KEY: primer_bind
<222> LOCATION: (1)..(18)
<223> OTHER INFORMATION: Synthesized 16S rRNA reverse primer

<400> SEQUENCE: 8
gctgcctccc gtaggagt                                                   18

<210> SEQ ID NO 9
<211> LENGTH: 21
<212> TYPE: DNA
<213> ORGANISM: Human papillomavirus type 18
<220> FEATURE:
<221> NAME/KEY: primer_bind
<222> LOCATION: (1)..(21)
<223> OTHER INFORMATION: WalkID primer

<400> SEQUENCE: 9
gcgctgcagg catgcgagct c                                               21

<210> SEQ ID NO 10
<211> LENGTH: 34
<212> TYPE: DNA
<213> ORGANISM: Human papillomavirus type 18
<220> FEATURE:
<221> NAME/KEY: primer_bind
<222> LOCATION: (1)..(34)
```

<223> OTHER INFORMATION: WALKOL_EcoRI_I primer

<400> SEQUENCE: 10
gcgctgcagg catgcgagct cccaagcttg atcg          34

<210> SEQ ID NO 11
<211> LENGTH: 38
<212> TYPE: DNA
<213> ORGANISM: Human papillomavirus type 18
<220> FEATURE:
<221> NAME/KEY: primer_bind
<222> LOCATION: (1)..(38)
<223> OTHER INFORMATION: WALKOL_EcoRI_II primer

<400> SEQUENCE: 11
aattcgatca agcttgggag ctcgcatgcc tgcagcgc          38

<210> SEQ ID NO 12
<211> LENGTH: 24
<212> TYPE: DNA
<213> ORGANISM: Human papillomavirus type 18
<220> FEATURE:
<221> NAME/KEY: primer_bind
<222> LOCATION: (1)..(24)
<223> OTHER INFORMATION: WALKOL_HindIII primer

<400> SEQUENCE: 12
gcgctgcagg catgcgagct ccca          24

<210> SEQ ID NO 13
<211> LENGTH: 28
<212> TYPE: DNA
<213> ORGANISM: Human papillomavirus type 18
<220> FEATURE:
<221> NAME/KEY: primer_bind
<222> LOCATION: (1)..(28)
<223> OTHER INFORMATION: WALKOL_HindIII_II primer

<400> SEQUENCE: 13
agcttgggag ctcgcatgcc tgcagcgc          28

<210> SEQ ID NO 14
<211> LENGTH: 28
<212> TYPE: DNA
<213> ORGANISM: Human papillomavirus type 18
<220> FEATURE:
<221> NAME/KEY: primer_bind
<222> LOCATION: (1)..(28)
<223> OTHER INFORMATION: WALKOL_BglII primer

<400> SEQUENCE: 14
agcttgggag ctcgcatgcc tgcagcgc          28

<210> SEQ ID NO 15
<211> LENGTH: 34
<212> TYPE: DNA
<213> ORGANISM: Human papillomavirus type 18
<220> FEATURE:
<221> NAME/KEY: primer_bind
<222> LOCATION: (1)..(34)
<223> OTHER INFORMATION: WALKOL_BglII_II primer

<400> SEQUENCE: 15
gcgctgcagg catgcgagct cccaagcttg atcg          34

<210> SEQ ID NO 16
<211> LENGTH: 26

```
<212> TYPE: DNA
<213> ORGANISM: Artificial Sequence
<220> FEATURE:
<221> NAME/KEY: primer_bind
<222> LOCATION: (1)..(26)
<223> OTHER INFORMATION: Synthesized MR-fw primer (multi resistance
      gene)

<400> SEQUENCE: 16
caaactacgg taacattgat cgcaac                                          26

<210> SEQ ID NO 17
<211> LENGTH: 26
<212> TYPE: DNA
<213> ORGANISM: Artificial Sequence
<220> FEATURE:
<221> NAME/KEY: primer_bind
<222> LOCATION: (1)..(26)
<223> OTHER INFORMATION: Synthesized MR-Re primer (multi resistance
      gene)

<400> SEQUENCE: 17
caatatgtat gctttggtct ttctgc                                          26

<210> SEQ ID NO 18
<211> LENGTH: 25
<212> TYPE: DNA
<213> ORGANISM: Staphylococcus aureus
<220> FEATURE:
<221> NAME/KEY: primer_bind
<222> LOCATION: (1)..(25)
<223> OTHER INFORMATION: SA-fw primer

<400> SEQUENCE: 18
cgtgaagaaa cagaacgaat gattc                                           25

<210> SEQ ID NO 19
<211> LENGTH: 26
<212> TYPE: DNA
<213> ORGANISM: Staphylococcus aureus
<220> FEATURE:
<221> NAME/KEY: primer_bind
<222> LOCATION: (1)..(26)
<223> OTHER INFORMATION: SA-Re primer

<400> SEQUENCE: 19
gcctctagaa tatttcatcg catttg                                          26
```